(12) United States Patent
Meikle et al.

(10) Patent No.: US 8,097,431 B2
(45) Date of Patent: Jan. 17, 2012

(54) METHODS AND COMPOSITIONS FOR DETECTING STEROIDS

(75) Inventors: A. Wayne Meikle, Salt Lake City, UT (US); David J. Stillman, Salt Lake City, UT (US); Jared M. Orrock, Salt Lake City, UT (US); Alan H. Terry, Bountiful, UT (US); Tanya M. Sandrock, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 711 days.

(21) Appl. No.: 11/631,725

(22) PCT Filed: Aug. 4, 2005

(86) PCT No.: PCT/US2005/028071
§ 371 (c)(1),
(2), (4) Date: Oct. 7, 2008

(87) PCT Pub. No.: WO2006/017813
PCT Pub. Date: Feb. 16, 2006

(65) Prior Publication Data
US 2009/0035754 A1 Feb. 5, 2009

Related U.S. Application Data

(60) Provisional application No. 60/598,926, filed on Aug. 4, 2004.

(51) Int. Cl.
*G01N 33/53* (2006.01)
*C12Q 1/66* (2006.01)
*C12Q 1/48* (2006.01)
*C12Q 1/42* (2006.01)
*C07H 21/04* (2006.01)
*C12P 21/06* (2006.01)
*C12N 15/00* (2006.01)
*C12N 5/00* (2006.01)

(52) U.S. Cl. .......... 435/7.8; 435/8; 435/15; 435/21; 435/69.1; 435/320.1; 435/325; 435/810; 536/23.4; 536/23.5

(58) Field of Classification Search .............. None
See application file for complete search history.

(56) References Cited

U.S. PATENT DOCUMENTS

| | | | |
|---|---|---|---|
| 4,477,577 A * | 10/1984 | Nakamura et al. | 436/510 |
| 5,696,233 A | 12/1997 | Evans et al. | |
| 5,710,004 A | 1/1998 | Evans et al. | |
| 5,935,934 A | 8/1999 | Vegeto et al. | |
| 6,291,194 B1 * | 9/2001 | Raivio et al. | 435/7.1 |
| 6,387,673 B1 | 5/2002 | Evans et al. | |
| 6,551,773 B1 | 4/2003 | Evans et al. | |
| 6,576,422 B1 | 6/2003 | Weinstein et al. | |
| 6,673,596 B1 | 1/2004 | Sayler et al. | |
| 7,037,656 B2 | 5/2006 | Tran et al. | |
| 7,074,566 B2 * | 7/2006 | Wolf et al. | 435/6 |
| 7,091,038 B2 * | 8/2006 | Palli et al. | 435/320.1 |
| 7,153,685 B2 * | 12/2006 | Mao et al. | 435/325 |
| 2003/0077664 A1 * | 4/2003 | Zhao et al. | 435/7.2 |

OTHER PUBLICATIONS

Giguere. 1999. Endocrine Rev. 20:689-725.*
http://chemistry.about.com/od/chemicalstructures/ig/Steroids/, downloaded Nov. 10, 2010.*
http://www.chm.bris.ac.uk/webprojects2002/schnepp/vitamind.html downloaded Nov. 10, 2010.*
http://www.colorado.edu/intphys/Class/IPHY3430-200/image/23-8 downloaded Nov. 10, 2010.*
Balasubramanian, B., et al., 1999, Binding of Gal4p and biocoid to nucleosomal sites in yeast in the absence of replication. *Mol. Cell Biol.* 19(4): 2977-2985.
Beck, V., E. et al., 2003, Comparison of hormonal activity (estrogen, androgen and progestin) of standardized plant extracts for large scale use in hormone replacement therapy. *J. Steroid Biochem. Mol. Biol.* 84: 259-268.
Berghofer-Hochheiner, Y., et al., 1997, Expression of the vitamin D and the retinoid X receptors in *Saccharomyces cerevisiae*: alternative in vivo models for ligand-induced transactivation. *J. Cell Biochem.* 66: 184-196.
Evans, R. M., 1988, The steroid and thyroid hormone receptor superfamily. *Science* 240: 889-895.
Gaido, K. W., et al., 1997, Evaluation of chemicals with endocrine modulating activity in a yeast-based steroid hormone receptor gene transcription assay. *Toxicol. Appl. Pharmacol.* 143: 205-212.
Gao, C. Y. et al., 2000, Tightly regulated, beta-estradiol does-dependent expression system for yeast. *Biotechniques* 29(6): 1226-1231.
Gong, Y., et al., 2003, Clustering of sex hormone disruptors in Singapore's marine environment. *Environ. Health Perspect.* 111: 1448-1453.
Jin, C. H. et al., 1996, Human vitamin D receptor-dependent transactivation in *Saccharomyces cerevisiae* requires retinoid X receptor. *Mol. Endocrinol.* 10: 196-205.

(Continued)

*Primary Examiner* — Shulamith H Shafer
(74) *Attorney, Agent, or Firm* — Foley & Lardner LLP

(57) ABSTRACT

The present invention provides for methods and systems for detecting steroids. Examples of such steroids include estrogen, progesterone, androgen, testosterone, and derivatives and analogs thereof. Systems useful for carrying out the method include tripartite constructs including a DNA-binding domain, a ligand binding domain, and an activation domain. The present invention provides numerous improvements over previous diagnostic systems for detection of steroids, such advantages include that the method allows for detection of steroid analogs and derivatives, whose structures may not yet be known, the method is generally applicable to a wide variety of organisms, and numerous ligand binding domains may be used in conjunction with the present system.

12 Claims, 8 Drawing Sheets

OTHER PUBLICATIONS

Klein, K. O. et al., 1998, Use of an ultrasensitive recombinant cell bioassay to determine estrogen levels in girls with precocious puberty treated with a luteinizing hormone-releasing hormone agonist. *J. Clin. Endocrinol. Metab.* 83(7): 2387-2389.

Klein, K. O., et al., 1994, Estrogen levels in childhood determined by an ultrasensitive recombinant cell bioassay. *J. Clin. Invest.* 94: 2475-2480.

Klein, K. O. et al., 1995, Use of ultrasensitive recombinant cell bioassay to measure estrogen levels in women with breast cancer receiving the aromatase inhibitor, letrozole. *J. Clin. Endocrinol. Metab.* 80(9): 2658-2660.

Klein, K. O. et al., 1999, Estrogen levels in girls with premature thelarche compared with normal prepubertal girls as determined by an ultrasensitive recombinant cell bioassay. *J. Pediatr.* 134: 190-192.

Kuhn, C. M., 2002, Anabolic steroids. *Recent Prog. Horm. Res.* 57: 411-434.

Larmore K. A. et al., 2000, Estradiol suppression and recovery during leuprolide acetate treatment in women as determined weekly by an ultrasensitive recombinant cell bioassay. *Gynecol. Endocrinol.* 14: 405-410.

Lee, H. J., et al., 2003, Novel yeast bioassay system for detection of androgenic and antiandrogenic compounds. *Toxicol. In Vitro* 17: 237-244.

Louvion, J. F., et al., 1993, Fusion of GAL4-VP16 to a steroid-binding domain provides a tool for gratuitous induction of galactose-responsive genes in yeast. *Gene* 131: 129-134.

Mauras, N., et al., 2000, Estrogen suppression in males: metabolic effects. *J. Clin. Endocrinol. Metab.* 85(7): 2370-2377.

McKenna, N. J., et al., 1999, Nuclear receptor coregulators: cellular and molecular biology. *Endocr. Rev.* 20(3): 321-344.

Mumberg, D., R. et al., 1994, Regulatable promoters of *Saccharomyces cerevisiae*: comparison of transcriptional activity and their use for heterologous expression. *Nucleic Acids Res.* 22: 5767-5768.

Mumberg, D., et al., 1995, Yeast vectors for the controlled expression of heterologous proteins in different genetic backgrounds. *Gene* 156: 119-122.

Pajic, T., et al., 1999, Biotransformation of steroids by the fission yeast *Schizosaccharomyces pombe*. *Yeast* 15: 639-645.

Paris, F. N. et al., 2002, A new Recombinant cell bioassay for ultrasensitive determination of serum estrogenic bioactivity in children. *J. Clin. Endocrinol. Metab.* 87: 791-797.

Raivio et. al., *J. Clin. Endocrinol. Metab.* 86 (3): 1539-1544 (2001).

Ronicke, V., et al., 1997, Use of conditional promoters for expression of heterologous proteins in *Saccharomyces cerevisiae*. *Methods Enzymol.* 283: 313-322.

Shiraishi, F., et al., 2003, Estrogenic and thyroid hormone activity of a series of hydroxyl-polychlorinated biphenyls. *Chemosphere* 52: 33-42.

Soto, A. M., et al., 1995M The E-Screen assay as a tool to identify estrogens: an update on estrogenic environmental pollutants. *Environ. Health Perspect.* 103 Suppl 7: 113-122.

Walfish, P. G., et al., 1997, Yeast hormone response element assays detect and characterize GRIP1 coactivator-dependent activation of transcription by thyroid and retinoid nuclear receptors. *Proc. Natl. Acad. Sci. USA* 94: 3697-3702.

Wang, Y., et al., 1994, A regulatory system for use in gene transfer. *Proc. Natl. Acad. Sci. USA* 91: 8180-8184.

International Search Report and Written Opinion for International Application No. PCT/US2005/028071 dated Jun. 20, 2008.

* cited by examiner

A. Androgen Cells BioRad 040302

B. Estrogen Cells BioRad 040302

C. Progesterone Cells BioRad 040302

METHODS AND COMPOSITIONS FOR DETECTING STEROIDS

CROSS REFERENCE TO RELATED APPLICATIONS

The present application is a U.S. national phase filing under 35 U.S.C. 371 of PCT application No. PCT/US2005/08071, filed Aug. 4, 2005, which claims the benefit of U.S. Provisional Patent Application No. 60/598,926, filed Aug. 4, 2004, each of which are hereby incorporated by reference in their entirety.

FIELD OF THE INVENTION

The present invention relates to novel screening methods and systems for detecting and quantifying steroids, where such steroids may have the classical chemical structure:

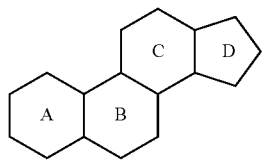

More specifically, a yeast-based expression system facilitates the screening of agents capable of activating a steroid hormone receptor.

BACKGROUND OF THE INVENTION

There are numerous reasons to monitor hormone levels of an individual. Medically, physicians may choose, for example, to monitor progesterone and/or estrogen levels of women receiving hormone replacement therapy; androgen levels of men treated for prostate cancer; hormone levels of children with pituitary disorders; or progesterone levels of pregnant women. Sociologically, public officials and government agencies must address increasing concerns that chemicals in the environment, such as pesticides and fungicides, are affecting human health. Financially, professional sports organizations, charged with maintaining fair competition, routinely test athletes and racehorses for anabolic steroids which may influence the distribution of prizes.

Testing procedures currently used to detect anabolic steroids in professional athletes and racehorses require column chromatography to remove water, ions, and proteins from urine. The purified steroids are then chemically modified to make them more volatile for gas chromatography-mass spectrometry (GC-MS) analysis. An algorithm is used to search for 30-40 banned steroids based on CG retention time and two or three ions per molecule in the mass spectrum. This detection method is expensive and fallible. Automated purification systems, gas chromatographs and mass spectrometers are costly and technically complicated laboratory instruments that must be continually calibrated and operated by trained technicians in order to produce reliable results. Additionally, this method identifies only 30-40 of the literally hundreds of possible molecules in the steroid family. A person skilled in the chemical arts could easily derivatize a banned steroid to create a previously unknown or uncategorized molecule with potent physiological properties. The derivatized steroid would go undetected by the currently used method because the GC retention time and/or ions of the mass spectrum would not match those searched by the algorithm.

Quantitative determinations of anabolic steroids are complicated by the fact that steroids are ubiquitous in the human body. For example, urinanalysis for exogenous testosterone typically measures the ratio of testosterone to epitestosterone, but athletes wishing to beat a steroid test can simply counter their testosterone intake with a proportional intake of epitestosterone such that the ratio remains constant.

Steroids may also be detected through bioassay; however, currently available bioassays lack critical sensitivity and accuracy. For example, Raivio et al. (JCE&M, 86: 3, 2001, 1539) reported an assay for measuring androgen bioactivity in human serum. The assay consisted of a) a Gal4 DNA-binding domain operably linked to an androgen receptor ligand binding domain (Gal4-DBD:AR-LBD); b) a herpes simplex VP16 protein operably linked to the N-terminal region of the androgen receptor (VP16:AR(N terminus)), c) a luciferase reporter gene and d) an AR-interacting protein 3 (ARIP3) for amplification. Unfortunately, the constructs were incapable of detecting steroids with sufficient sensitivity or specificity to be useful as an assay.

Paris and colleagues (J. Clin. Endocrinol. Metab. 87: 2002, 791) also developed a bioassay with virtually no diagnostic utility. They reported an estrogen bioassay that employed recombinant HeLa cells expressing the estrogen receptor with an estrogen response element driving a luciferase reporter. However, HeLa cells contain endogenous aromatase, an enzyme that converts testosterone to estrogen. Although aromatase inhibitors may be added to the cells in an attempt to eliminate the endogenous conversion of testosterone, it is unconfirmed whether or not such an assay would provide a reliable means of detection.

Balasubramanian and Morse (Mol. Cell Biol. 19: 2977-2985) reported a tripartite construct (LexA-DBD:ER-LBD:VP16) in yeast useful in their studies of transcriptional activators. However, the use of a yeast based system and construct in a clinical diagnostics setting for the detection and monitoring of various steroids was not contemplated, presumably due to inherent challenges created by other components in serum, such as metals, sugars, and amino acids that affect yeast growth or the ability to detect the downstream reporter. Attempts to remove such factors, such as by extraction, can also bias the sample and make the results unreliable. Use of a yeast system in a bioassay also has inherent challenges due to endogenous properties of the yeast cells themselves, such as bioconversion of the steroids being assayed and factors affecting transcription efficiency, such as cross-reactivity issues, transport issues, and transcriptional issues.

A simple method of measuring steroids in a clinical setting is greatly needed. Currently, there are no affordable, sensitive, reliable and versatile methodologies capable of detecting steroids or other molecules capable of binding a steroid hormone receptor.

SUMMARY OF THE INVENTION

The present invention provides systems and methods for identifying and quantifying steroids. Steroids detectable by the present invention include sex steroids, such as estrogen, progesterone, androgen, testosterone, and derivatives and analogs thereof. Additionally, any molecule that binds a steroid hormone receptor is also capable of being detected by the methods of the present invention.

In one embodiment, the system of the present invention includes a tripartite construct including a DNA binding domain (DBD), a ligand binding domain (LBD) comprising a steroid hormone receptor, and an activation domain (AD). In a particular embodiment, the DBD may be LexA. In another embodiment, the LBD may be selected from the group consisting of an estrogen receptor (ER)-LBD, an androgen receptor (AR)-LBD, a progesterone receptor (PR)-LBD and the like. In one particular embodiment, the activation domain may be VP16.

In another embodiment, the tripartite construct is inserted into a plasmid which is expressed in a yeast host cell. The fusion protein confers steroid-responsive transcription of a reporter gene, that encodes an easily measured enzyme, such as β-galactosidase or luciferase. The enzyme may be quantified by known techniques and related to the amount of steroid present in a sample. In another embodiment, the fusion protein confers steroid-responsive transcription of a gene that encodes a protein easily measured electrochemically.

In another embodiment, methods of the present invention include selecting a DNA binding domain capable of preferentially binding to a specific host DNA locus and activating expression of that gene; further selecting a ligand binding domain including a portion of a steroid hormone receptor; further selecting an activation domain; operably linking the DNA binding domain to the ligand binding domain; and operably linking the ligand binding domain to the activation domain to create a tripartite construct. The tripartite construct is then ligated into an expression vector and introduced into a target host cell where at least one host cell exhibiting expression of the DNA construct is identified.

In another embodiment, binding of a steroid to the hormone receptor ligand binding domain activates the tripartite protein. The activated protein may then enter the nucleus where the DNA-binding domain of the construct may bind to genomic DNA in the nucleus. Alternatively, the activated protein may bind DNA on a plasmid or fragments of DNA, either in the nucleus or cytoplasm of the host cell. Binding of the tripartite construct to DNA may activate transcription of a reporter gene, wherein the transcription product of said reporter gene may be detected by techniques known to those skilled in the biochemical arts.

In an embodiment of the present invention, cross-reactivity is minimized such that multiple tripartite systems may be used at the same time to detect different steroids present in a single sample.

In another embodiment of the present invention, coactivators such as GRIP1 and RIP140 may be used to enhance ligand-dependent transactivation.

In yet another embodiment, the present invention can be utilized to monitor steroid levels of an individual. For example, a steroid bioassay could be used to measure progesterone and/or estrogen levels of women receiving hormone replacement therapy or birth control; androgen levels of men treated for prostate cancer; hormone levels of children with pituitary disorders; progesterone levels of pregnant women; and/or testosterone levels of athletes or racehorses as a test for anabolic steroid abuse.

In another embodiment, the present invention may be used to test industrial chemicals, household chemicals, pesticides, fungicides, fertilizers and the like for affects on hormone receptors. A test of this type could provide scientific evidence regarding whether or not specific chemicals in the environment may be linked to infertility, late onset puberty, birth defects, or other hormonal dysfunctions. Activation of the steroid receptor by a pesticide, for example, would suggest that that particular pesticide may be involved in hormonal dysfunctions, including hormone-responsive cancers.

In another embodiment, the present invention may be used in the pharmaceutical industry to screen new compounds for steroidal activity.

In still another embodiment, the present invention provides for monitoring of molecules with steroid activity in serum, saliva, saline, urine or other appropriate medium.

In yet another embodiment of the present invention, the system may be utilized in numerous types of eukaryotic and prokaryotic cells including but not limited to mammalian, Cos-7, HeLa, yeast and bacteria cells.

Many alterations and variations of the invention exist as described herein. The elements necessary to carry out the methods and produce the compositions of the present invention as herein disclosed can be adapted for application in any cell or organism. The invention provides a general method for detection of steroids using a yeast-based, ligand-dependent reporter system.

BRIEF DESCRIPTION OF THE DRAWINGS

The following drawings form part of the present specification and are included to further demonstrate certain embodiments. These embodiments may be better understood by reference to one or more of these drawings in combination with the detailed description of specific embodiments presented herein.

DEFINITIONS

Figure 1:
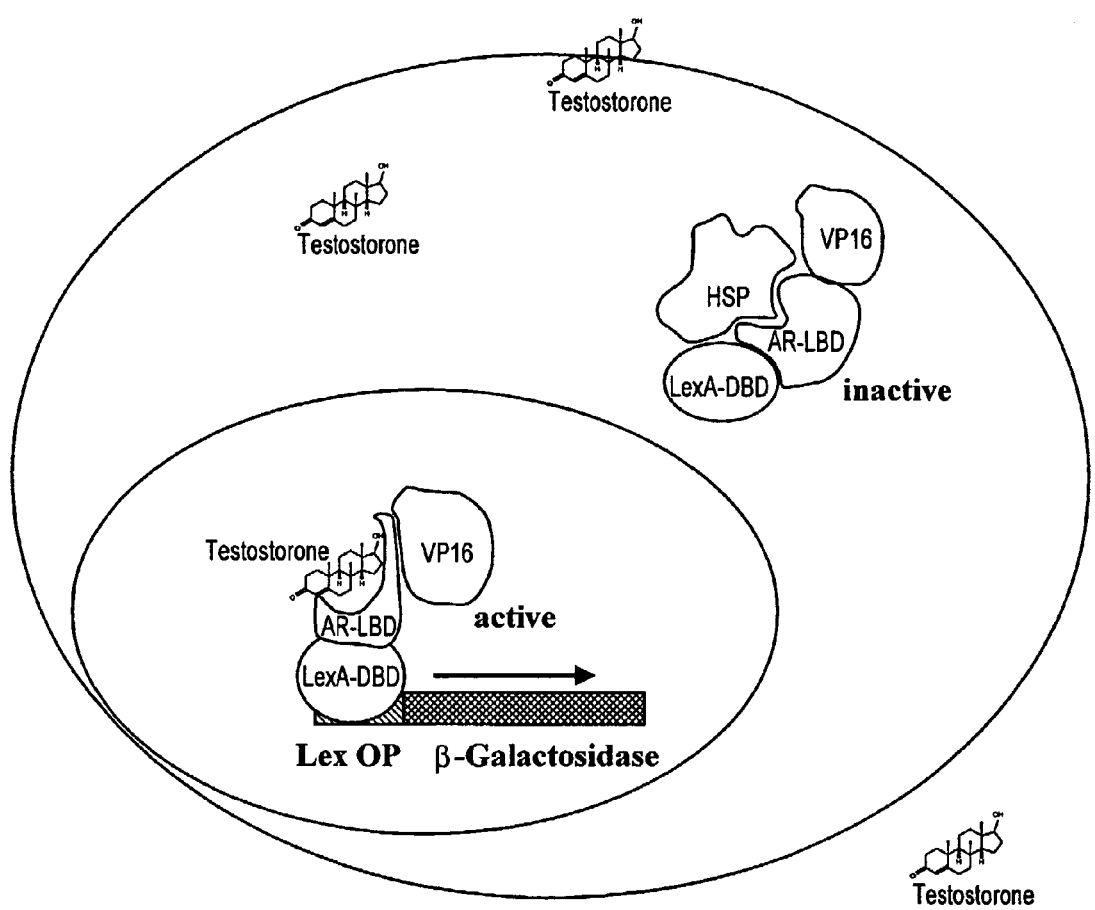
FIG. 1 illustrates a schematic tripartite system according to an embodiment of the present invention.

For the purposes of the present invention, the following terms shall have the following meanings:

As used herein, the term "steroid" refers to steroid hormones, such as sex hormones including but not limited to estrogen, progesterone, androgen, testosterone, dihydrotestosterone, 5-androdiol, nandrolone (Deca), estradiol, oxymethalone, oxyandrolone, boldenone (equipoise), methandrostenalone (dianabol, Dbol), stanozolol, trenbolone, mesterolone, masteron, halotestin (fluoxymesterone) and derivatives and analogs thereof. Further steroids that may be detected by the compositions and methods of the present invention include both natural and synthetic steroids and derivatives and analogs thereof. Additionally, for the purposes of the present invention, the terms "steroid" and "ligand" shall be used interchangeably to refer to any molecule capable of binding to a nuclear hormone receptor. Such molecules include but are not limited to chemical molecules, peptides, peptide fragments, steroids and derivatives or analogs thereof. Through interaction with ligand binding domains, ligands change the conformation of the protein and thereafter activate or inactivate the tripartite systems.

For the purposes of the present invention, the terms "nuclear hormone receptor", "steroid hormone receptor" and "ligand binding domain" shall be used interchangeably. Receptors are portions of protein that selectively bind steroids or ligands. Receptors may be those isolated from nature; variants or analogs of those found in nature; or those designed by the hand of man. "Steroid hormone receptors" may also refer to receptors known to selectively bind steroid hormone inhibitors.

For the purposes of the present invention, the term "protein" shall include fragments of proteins, peptides, polypeptides, and the like.

As used herein, the term "reporter gene" refers to a gene that encodes an enzyme or protein whose expression may be assayed; such proteins include, but are not limited to, β-galactosidase (LacZ), β-glucuronidase (GUS), alkaline phosphatase, amino acid biosynthetic genes, e.g., the yeast LEU2, HIS3, or LYS2 genes, nucleic acid biosynthetic genes, e.g., URA3 or ADE2 genes, the chloramphenicol acetyltransferase (CAT) gene, the green fluorescent protein (GFP), red fluorescent protein, orange fluorescent protein or any surface antigen gene for which specific antibodies are available. Additionally, reporter genes may encompass any gene of interest whose expression product may be detected.

As used herein, the terms "host cell" or "host organism" or, simply, "target host", refer to any organism or cell line that is the recipient of a cloning or expression vector. In one embodiment, the host cell of the invention is a yeast cell or a cultured animal cell, such as a mammalian cell. In another embodiment, the yeast host cell is Saccharomyces cerevisiae or a modified yeast cell (e.g., a knock-out Saccharomyces cerevisiae). In another embodiment, the yeast host cell includes introduced background mutations that enhance the detection of the steroid, such as host cells that express genes involved in steroid metabolism, host cells with knocked out or inactivated multiple drug resistant (MDR) genes, thus increasing import of steroids into yeast, or host cells with knocked out, inactivated or otherwise modified transcriptional regulatory genes, thus improving the sensitivity or dynamic range of the assay.

As used herein, a "promoter" is a DNA sequence located proximal to the start of transcription at the 5' end of an operably linked transcribed sequence. The promoter may contain one or more regulatory elements or modules which interact in modulating transcription of the operably linked gene. An inducible promoter is a promoter which responds to the presence of different biochemical stimuli. Such promoters include, but are not limited to, the CUP1 promoter, heat shock promoters, galactose-inducible promoters and the like.

For the purposes of the present invention, the term "operably linked" describes two macromolecular elements arranged such that modulating the activity of the first element induces an effect on the second element. In this manner, modulation of the activity of a promoter element may be used to alter and/or regulate the expression of an operably-linked coding sequence. For example, the transcription of a coding sequence that is operably-linked to a promoter element is induced by factors that "activate" the promoter's activity; transcription of a coding sequence that is operably-linked to a promoter element is inhibited by factors that "repress" the promoter's activity. Thus, a promoter region is operably-linked to the coding sequence of a protein if transcription of such coding sequence activity is influenced by the activity of the promoter.

For the purposes of the present invention, the term "construct" refers generally to recombinant genes which encode fusion proteins. A "fusion protein" is a hybrid protein, i.e., a protein which has been constructed to contain domains from at least two different proteins. For the purposes of the present invention, a fusion protein is a hybrid protein which possesses (a) a transcriptional regulatory domain (e.g., transcriptional activation domain) from a transcriptional regulatory protein, and/or (b) a DNA binding domain from a DNA binding protein linked to a heterologous protein to be assayed for interaction. The structure of the fusion protein is such that the transcriptional regulatory domain and the DNA binding domain are arranged in a manner that allows both domains to be biologically active. The protein that is the source of the transcriptional regulatory domain is different from the protein that is the source of the DNA binding domain. In other words, at least two domains within a protein are heterologous to each other.

The transcriptional regulatory domain of the fusion protein may either activate or repress transcription of target genes, depending on the native biological activity of the domain. For the purposes of the present invention, the term "transactivate" shall refer to activation of transcription. In a particular embodiment of the present invention, an estrogen molecule interacts with a fusion protein encoding LexA:(ER)-LBD: VP16, thus inducing protein folding that eliminates binding of inhibitory molecules, allowing the VP16 transcriptional regulatory domain to become functionally active. Activation of the VP16 regulatory domain allows for transcription of a reporter gene that encodes a detectable protein.

For the purposes of the present invention, the term "expression" relates to the process by which the information encoded within a gene is revealed. If the gene encodes a protein, expression involves both transcription of the DNA into mRNA, the processing of the mRNA (if necessary) into a mature mRNA product, and translation of the mature mRNA into protein. A nucleic acid molecule, such as a DNA or gene is said to be "capable of expressing" a polypeptide if the molecule contains the coding sequences for the polypeptide and the expression control sequences which, in the appropriate host environment, provide the ability to transcribe, process and translate the genetic information contained in the DNA into a protein product, and if such expression control sequences are operably-linked to the nucleotide sequence that encodes the polypeptide.

For the purposes of the present invention, the term "marker" refers to a gene or sequence whose presence or absence conveys a detectable phenotype to the host cell or organism. Various types of markers include, but are not limited to, selection markers, screening markers and molecular markers. Selection markers are usually genes that can be expressed to convey a phenotype that makes an organism resistant or susceptible to a specific set of environmental conditions. Screening markers can also convey a phenotype that is a readily observable and distinguishable trait, such as Green Fluorescent Protein (GFP), GUS or β-galactosidase. Molecular markers are, for example, sequence features that can be uniquely identified by oligonucleotide probing, for example RFLP (restriction fragment length polymorphism), or SSR markers (simple sequence repeat).

As used herein, the terms "expression vector" and "expression plasmid" refer to a vehicle or vector that is capable of delivering a nucleic acid sequence into a host cell for replication purposes. In some instances, an expression vector is integrated into the host chromosome and replicates with chromosomal DNA, while in other instances the expression vector is an episomal plasmid that replicates extrachromosomally.

Expression vectors are especially designed to provide an environment which allows the expression of the cloned gene after transformation into the host. One manner of providing such an environment is to include transcriptional and translational regulatory sequences on such expression vectors, such transcriptional and translational regulatory sequences capable of being operably linked to the cloned gene. Another manner of providing such an environment is to provide a cloning site or sites on such vector, wherein a desired cloned gene and desired expression regulatory elements may be cloned. In an expression vector, the gene to be cloned is usually operably-linked to certain control sequences such as promoter sequences. Expression control sequences will vary depending on whether the vector is designed to express the operably-linked gene in a prokaryotic or eukaryotic host and may additionally contain transcriptional elements such as enhancer elements, termination sequences, tissue-specificity elements, and/or translational initiation and termination sites.

For the purposes of the present invention, the term "sequence" means any series of nucleic acid bases or amino acid residues, and may or may not refer to a sequence that encodes or denotes a gene or a protein. Many of the genetic constructs used herein are described in terms of the relative positions of the various genetic elements to each other. For the purposes of the present invention, the term "adjacent" is used to indicate two elements that are next to one another without implying actual fusion of the two elements, as there can be intervening, non-specified DNA between a given sequence and its adjacent sequences. These and other terms used to describe relative position are used according to normal accepted usage in the field of genetics. Numerous modifications, insertions and deletions may be made to the sequences of the present invention and still the result will fall within the spirit and scope of the invention as disclosed herein. For example, conservative substitutions within a sequence, (e.g., valine for glycine, arginine for lysine, etc.) or non-conservative substitutions, deletions, or insertions located at positions of the amino acid sequence which do not destroy the function of the protein may be used to create an amino acid sequence that is "substantially identical" with a sequence explicitly disclosed herein. All such modifications, insertions and deletions are contemplated.

Moreover, for the purposes of the present invention, the term "a" or "an" entity refers to one or more than one of that entity; for example, "a protein" or "an nucleic acid molecule" refers to one or more of those compounds, or at least one compound. As such, the terms "a" or "an", "one or more" and "at least one" can be used interchangeably herein. It is also to be noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated or biologically pure compound is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis.

Tripartite Constructs

Tripartite constructs are produced when three DNA domains are operably linked and at least two of the domains derive from different sources (i.e, at least two of the domains are heterologous). For the purposes of the present invention, tripartite constructs are produced by the sequential combination of:

(1) a DNA Binding Domain (DBD): a DNA binding domain is a protein domain capable of binding to DNA to activate transcription of a reporter gene. DNA binding domains of use with the present invention include but are not limited to LexA and Gal4.

(2) a Ligand Binding Domain (LBD): a ligand binding domain or steroid hormone receptor is a protein domain capable of specifically binding steroids or steroid-like compounds, or other proteins or compounds of interest. Binding of a ligand to the LBD induces folding of the fusion protein and eliminates binding of the inhibitor, allowing the AD bound to the promoter via the DBD to become functionally active. Examples of suitable ligand binding domains include ligand binding domains from any of the superfamily of nuclear receptors, including but not limited to estrogen receptors (ER)-LBD, an androgen receptors (AR)-LBD, a progesterone receptors (PR)-LBD, glucocorticoid receptors (GR)-LBD, mineralocorticoid receptors (MR)-LBD, all-trans retinoic acid receptors (RAR)-LBD, 9-cis retinoic acid receptors (RXR)-LBD, vitamin D receptors (VDR)-LBD, thyroid hormone receptors, ecdysone receptors (EcR)-LBD and orphan receptors.

Ligands or steroids that may bind to the ligand binding domain include but are not limited to estrogen, progesterone, androgen, testosterone, dihydrotestosterone (DHT), androstenedione, dehydroepiandrosterone (DHEA), estradiol, hydroxyflutamide, coumestrol, (DES), p-nonylphenol, bisphenol A, nafoxidine, o,p-DDE, clomiphene, ICI164,384, B-Sitosterol, methoxychlor, o,p-DDT, o,p-DDD, methyltestosterone, fluoxymesterone, oxymethelone, oxandrolone, methenolone acetate, danazole, 5a-androstan-17β-ol-3-one, methandrostenolone, hydroxyecdysone, and derivatives and analogs thereof. One of skill in the art will further appreciate that a LBD of the present invention may be interpreted broadly to include non-steroid proteins or chemicals.

(3) an Activation Domain (AD): an activation domain is a protein domain that, when relieved of the inhibition caused by factors bound by the DBD, stimulates the tripartite system to activate transcription of the reporter gene. Examples of suitable activation domains include but are not limited to VP16 (aa 424-490).

Numerous tripartite constructs, which may nominally be described as DBD:LBD:AD, may be created by mixing and matching domains. For example, two estrogen tripartite systems, LexA:(ER)-LBD:VP16 and Gal4:(ER)-LBD:VP16, may be created by exchanging DBD's. Likewise, various systems for probing different hormones may be created by exchanging LBD's (e.g., LexA:(ER)-LBD:VP16, LexA:(TR)-LBD:VP16, LexA:(PR)-LBD:VP16). Methods and techniques for carrying out these modifications will be readily apparent to one skilled in the biochemical arts.

One of skill in the art will also appreciate that a tripartite construct may include a ligand-binding domain whose specificity has been altered by mutagenesis. In a particular embodiment, directed or random mutagenesis is applied to select for constructs with increased selectivity to its known substrate, to provide a more highly sensitive assay. In another embodiment, directed or random mutagenesis is applied to select for constructs with increased selectivity to other substrates, such as a derivative of the known substrate, to provide a broader spectrum of bioassays.

One of skill in the art will also appreciate that tripartite constructs specific to other molecules may be formed by inserting short ligand binding regions of other proteins in loop regions of the nuclear receptor such that upon binding of the substrate the reporter is activated in a regulated manner by displacement of the heat shock protein.

DETAILED DESCRIPTION OF THE INVENTION

The present invention relates to methods and systems for detecting steroids. In contrast to previously known methods for steroid detection, the present invention is able to detect derivatives and analogs of naturally occurring steroids. Any molecule that binds with the ligand binding domain of the tripartite construct can be detected by the method of the present invention. Thus the invention provides for detection of previously unknown molecules that affect the steroid hormone receptor. Such molecules may include derivatives of anabolic steroids being manufactured as athletic performance aids.

The systems and methods of the present invention provide for use of short nucleic acid sequences in each of three domains forming the tripartite system. Advantageously, the use of short nucleic acid sequences encoding these protein domains makes it unnecessary to make and manipulate entire proteins for each portion of the construct. Additionally, the tripartite systems of the present invention are extremely versatile because various tripartite constructs may be created by mixing and matching domains.

Assay Methods and Kits

In a particular embodiment, the expression plasmids of the invention may be used in the generation of cell lines or cellular systems that express the proteins described herein. Such cell lines exhibiting ligand-dependent transactivation pathways may be used to identify molecules that impact the steroid hormone receptor transactivation pathway. This expression system has utility in methods for assaying materials for agonistic or antagonistic activity toward the steroid hormone receptor of interest in each system. For example, assays may be established whereby intact cells expressing the proteins of the invention are contacted with agents or materials suspected of affecting the intracellular activity of the steroid hormone receptor, and the affect of such agents on ligand-dependent transactivation activity measured. The effect of such agents on the ligand-dependent transactivation activity may be measured in any number of ways. For example, such cell systems may utilize a reporter system in which the production of the reporter signal is dependent on ligand-dependent transactivation. Numerous reporters may serve equally well in this application including, but not limited to, β-galactosidase, alkaline phosphatase, fluorescent green protein, luciferase and the like.

Assays involving the cell based systems of the invention may be formatted in any number of configurations. Particularly useful for evaluating large numbers of agents and materials are high throughput screening formats. Traditionally, such assays were typically formatted in 96 well plates. However, 384, 864, 1536 and larger well plates may be used in such high throughput assay systems. These systems are often automated using robotic technologies to allow manipulation and processing of large numbers of samples. The agents or materials that may be evaluated in the various assay methods of the invention for potential agonistic or antagonistic affects include but are not limited to small molecules, polymers, peptides, polypeptides, proteins, immunoglobulins or fragments thereof, oligonucleotides, antisense molecules, peptide-nucleic acid conjugates, ribozymes, polynucleotides and the like.

Biochips, DNA chips or DNA microarrays can also be used with the present invention. A "biochip" comprises a suitable solid substrate. By "substrate" or "solid support" or other grammatical equivalents herein is meant any material that can be modified to contain discrete individual sites appropriate for the attachment or association of the tripartite constructs, either as part of a plasmid or used alone, and amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably fluoresce. Generally the substrate is planar, although as will be appreciated by those in the art, other configurations of substrates may be used as well. For example, the probes may be placed on the inside surface of a tube, for flow-through sample analysis to minimize sample volume. Similarly, the substrate may be flexible, such as a flexible foam, including closed cell foams made of particular plastics.

In a particular embodiment, the surface of the biochip and the probe (i.e., tripartite system or tripartite construct) may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly useful. Using these functional groups, the probes can be attached using functional groups on the probes, for example using linkers as are known in the art. In addition, in some cases, additional linkers, such as alkyl groups (including substituted and heteroalkyl groups) may be used.

In a particular embodiment, a biochip includes various tripartite systems of the present invention such that a single biochip may be used to screen for estrogen, progesterone, testosterone, androgen, etc. and each steroid may be monitored in duplicate, triplicate or higher frequency. The tripartite systems may be attached to the biochip by techniques know to those skilled in the art.

Another configuration of the invention is the use of reporter genes that provide viability under selective growth conditions. Such reporter genes include, but are not limited to, the HIS3 and URA3 biosynthetic genes. Such viability selection assays can be used in a variety of schemes, including, but are not limited to, the identification of tripartite constructs with altered specificity in ligand recognition or the identification of new agonists. Expression of some reporter genes, including, but are not limited to, URA3 and CAN1, results in lethality when cells are grown in the presence of nontoxic compounds that are converted to a toxic compound by the enzyme encoded by the reporter genes. Such reporter genes and compounds that can be converted into toxic forms can be used in schemes to reduce expression of the reporter genes, allowing the identification of antagonists.

Another feature of the invention includes kits to facilitate the use of the compositions and methods disclosed herein. Exemplary kits would include the expression plasmids of the invention, and/or variants thereof. Also, included would be protocols for use of the compositions of the invention for the particular application and the necessary reagents to carry out the application. Such reagents may include, but are not limited to, buffers, solvents, media and solutions, substrates and cofactors, vectors and host cells, and detection or reporter reagents. Accessory items may include vials, vessels, reaction chambers and instructions.

Clinical Uses

Serum contains a myriad of components (i.e., sugars, amino acids, etc.) that may in some situations affect the assay. To at least partially circumvent potential inhibitory or non-specific effects, extracted samples may be tested. Steroids may be separated from serum by any method known in the art. In a particular embodiment, Strata-X solid phase extraction cartridges from Phenomenex (Torrence, Calif.) are used to partially purify steroids from serum.

Detection of Estrogen

The tripartite system may be used to monitor estrogen levels of per- or post-menopausal women, for example. Whole blood collected from the individual is separated and purified as described above. At least 3 aliquots of 50-200 μl extracted samples are added to a well plate. 50-200 μl of estrogen methanol is added to three unused wells, which will serve as controls running in triplicate. 100 μL of host cells, expressing the tripartite protein containing estrogen receptors and possessing DNA capable of expressing β-galactosidase, is added to each of the wells. The cells are grown at 30° C. in a shaking water bath or in a temperature controlled air incubator for 18 hr. 25 μl of cells from each well are transferred to a secondary well plate and 25 μl of Beta-Glo (Promega, Madison Wis.) are added to each well of the secondary plate. After 30 min incubation at room temperature, luminescence is detected using a Bio-Rad Lumimark luminometer. The detection level of the present invention is 10-1000 pg/ml. For comparison, the mean level of estradiol in healthy women is 50-150 pg/ml and in menopausal women is 10-20 pg/ml.

Detection of Progesterone

The tripartite system of the present invention may be used to detect and measure progesterone levels. Low progesterone levels have been linked to increased risk of miscarriage for pregnant women. Whole blood is drawn from an individual and processed as described above. In this embodiment, however, progesterone is used as the control and the host cells contain tripartite constructs with progesterone receptors rather than estrogen receptors. Progesterone levels detectable by this method range from 1000-100,000 pg/ml. During the first trimester of pregnancy, progesterone levels range from 10 to 90 ng/ml (10,000-90,000 pg/ml). For pregnant women with lower levels, physicians may prescribe progesterone therapy.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Yeast Strains and Methods

Yeast strain W303 yARUP16 MATa/MATα ade2-1/ade2-1, can1-100/can1-100, his3-11,151his3-11,15, trpl-1/trpl-1, ura3-1/URA3::Lex8op-lacZ, leu2-3,112/LEU2::Lex8op-Luciferase was transformed with plasmids encoding the various tripartite receptor fusion proteins (see Table 1) generating the mutants listed in Table 2. Lex8op contains 4 full operators or 8 half-lexA binding sites.

Chemicals

Danazole, 5a-dihydroT fluoxymesterone, methyl T, oxymethelone were purchased from Sigma (St. Louis, Mo.). Methenolone, testosterone, dihydrotestosterone, norethandrolone, stanozolol, oxandrolone, mesterolone, methenolone acetate, nandrolone, methandrostenolone, trans-dihydrotestosterone, methyldihydrotestosterone, androsterone, trans-dihydroandrosterone, epitestosterone, epiandrosterone, androstenediol, ethiocholanolone were purchased from Steraloids (Newport, R.I.). Androgen receptor inhibitors 1-(2-chlorophenyl)-1-(4-chlorophenyl)-2,2-dichloroethane and flutamide were purchased from Sigma, and cyproterone acetate was purchased from Steraloids (Newport, R.I.).

Extraction Methods

Total testosterone was extracted from serum using either ether or meth-tert butyl ether (MTBE). For ether extractions, 200 μl of serum was added to a 13-mm glass tube. 400 μl of ether was added to the serum and the tube was vortexed briefly. After a 5 min incubation at room temperature, the samples were centrifuged for 5 min at 2000 g and then placed at −80° C. for 30 min to freeze the aqueous layer. The liquid organic layer, containing the extracted testosterone, was transferred by pouring into a new glass tube. The ether was evaporated by incubating the samples at 60° C. To resuspend the testosterone, 350 μl of PBS containing 0.5% BSA was added to the tube. 50 μl of sample was added to 50 μl of cells for the bioassay.

Extraction with MTBE was similar except 1.25 ml of MTBE with 3% phosphoric acid was added to 200 μl of serum in a 2 ml eppendorf tube. The mixture was vortexed gently (at low setting). After a 5 min incubation, the tube was centrifuged at 17,000 g. After freezing the aqueous layer at −80° C., 750 μl of supernatant was transferred with a pippettman to a 13 mm glass tube. The solvent was the evaporated and the sample resuspended according to the ether extraction.

Solid Phase Extraction

To prepare serum samples for extraction, 500 ul, ninehundred microliters of serum was added to an equal volume of water. The tube was vortexed and heated for 5 min at 70° C. Solid phase extraction columns, Strata-X, 60 mg (phenomenex, Torrance, Calif.) were conditions with 1 ml of methanol followed by 1 ml of water. Sample was then applied to the column. The column was washed with 1 ml of water then vacuum was applied for 30 sec to remove residual water from the column. Steroids were eluted with 1 ml methanol; a vacuum was then applied for 30 sec to elute residual methanol. Fifty to one hundred microliters of eluent was added to each well in a 96-well plate and dried at 60° C.

Plasmids

FIG. 1 illustrates a schematic tripartite system according to an embodiment of the present invention. A yeast cell comprises an inactive LexA-DBD:AR-LBD:VP16-AD protein in the cytoplasm, which may be bound to a heat shock protein (HSP). Upon binding with an androgen that has crossed the cell membrane, the protein becomes activated and enters the nucleus. In the nucleus, the LexA end of the active tripartite system binds to a LexA binding site or operator (OP) of a lacZ reporter gene. This binding interaction activates transcription of β-galactosidase, which may be monitored via known luminescent detection techniques. Plasmid (lexA-DBD:ER:VP16) encoding the LexA DNA binding domain fused to estrogen response element and VP16 activation domain (LexA-DBD:ER-LBD:VP16) was obtained from Balasubramanian and Morse 1999. pARUP21 was generated by ligating the SpeI-XhoI fragment encoding the LexA-DBD:ER-LBD:VP16 fusion from plasmid lexA:ER:VP16 into SpeI-XhoI digested gel purified pRS413-GPD (Mumberg et al. 1994;

Mumberg et al. 1995; Ronicke et al. 1997). To make tripartite constructs with other LBD's, the estrogen receptor LBD was removed and other nuclear hormone receptors were cloned in frame between the LexA-DBD and VP16. The androgen receptor was amplified using primers oARUP61 (ggctgacatcggtcgacgcggtgtggaaatagatgggcttg) (SEQ. ID. NO. 11) and oARUP62 (ggggaattcccggggatcccatgtcagcccatctttctgaatg) (SEQ. ID. NO. 12) and p18, (Origene, Rockville Md.) as template (encoding the androgen receptor). The progesterone receptor was amplified using primers oARUP69 (ctgacatcggtcgacgctttatgaaagagaaggggtttcaccatccc) (SEQ. ID. NO. 13) and oARUP70 (cccggggatcccacagttgattccaccactgatcaacc) (SEQ. ID. NO. 14) using image clone 5167591 as template encoding the progesterone receptor (Invitrogen, Carlsbad, Calif.). The PCR fragments encoding the androgen and progesterone receptor ligand binding domains were digested with BamHI-SalI and ligated into the BamHI-SalI site of pARUP21 replacing the estrogen receptor with the androgen receptor (pARUP27) and progesterone receptor (pARUP32), respectively.

Liquid Bioassays

Yeast were inoculated from a plate into synthetic media lacking leucine, uracil and histidine supplemented with 2% dextrose. After 18 hr incubation at 30° C., cells were washed with synthetic media lacking leucine, uracil and histidine supplemented with glycerol and resuspended in glycerol media to an absorbance at 600 nm of 0.03. Cells were grown for 4 hr then 50 μL of cells were added to each well of a 96-well plate. 50 μl of steroid in phosphate buffered saline 0.5% BSA. Cells were grown at 30° C. in a shaking water bath for 18 hr. To detect β-galactosidase activity, 25 μl of cells and 25 μl of Beta-Glo (Promega, Madison Wis.) were transferred to a luminescent 96-well plate (Fisher, Pittsburgh, Pa.). After 30 min incubation at room temperature, the reaction mixture was read using Lumimark (Bio-Rad, Hercules, Calif.).

Alternatively, 100 μl of cells grown as described above were added to dry SPE extracted samples. The plate was covered with Aeroseal sealing film (Research Products International, Palatine Ill.). The cells were grown overnight and processed as described above.

Example 1

Creation of Androgen Inducible Expression System

Figure 2:
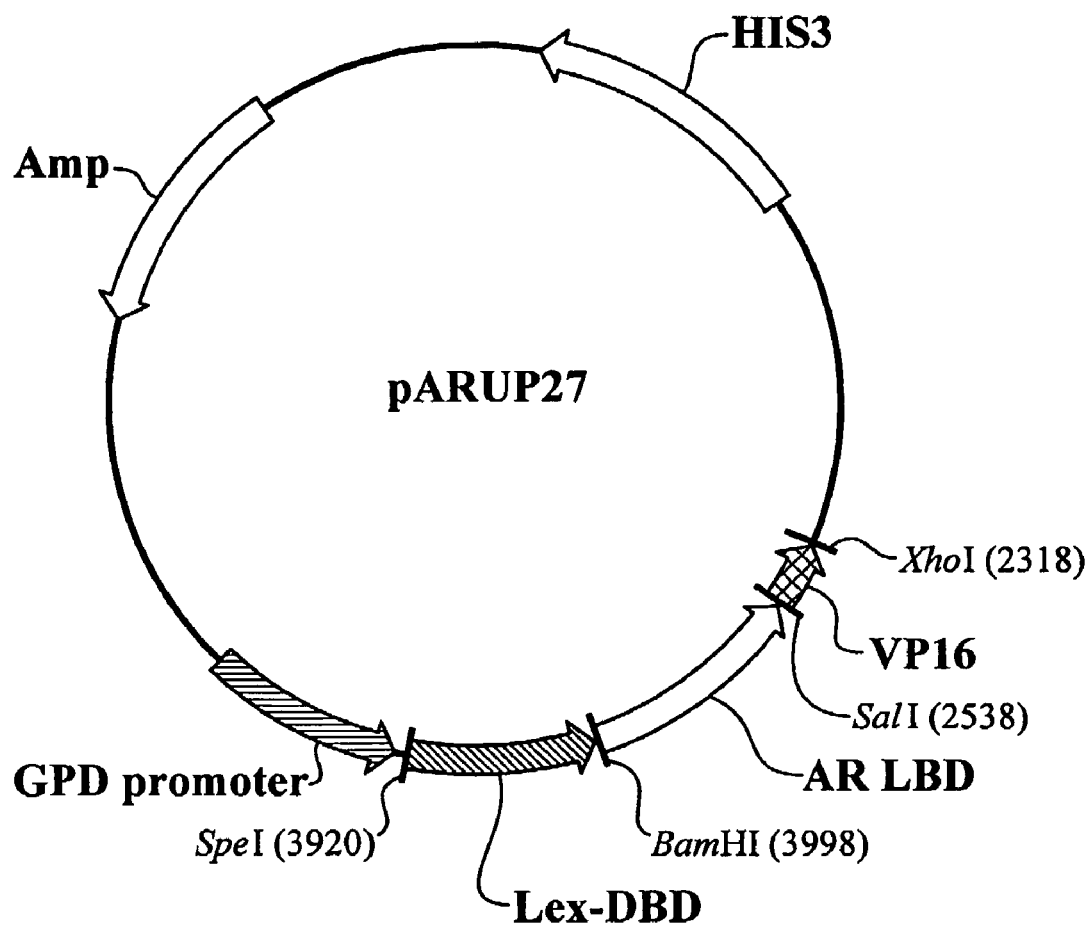
FIG. 2 illustrates a diagram of an androgen tripartite expression vector according to an embodiment of the present invention.

In order to generate an androgen inducible system, a fragment encoding the ligand-binding domain (amino acid residues 670-919) of the androgen receptor was inserted between the LexA DNA binding domain (LexA-DBD) and VP16 activation domain (a strong transcriptional activator encoded by the herpes simplex virus) creating pARUP27 (see FIG. 2). The (LexA-DBD:AR-LBD:VP16) fusion is driven by the strong constitutive glycerol-3-phosphate dehydrogenase (GPD) promoter. pARUP27 was transformed into yARUP16, a diploid yeast strain containing an integrated copy of each of two reporters, (lexA-8op-lacZ and LexA-8op-Luciferase). Both of these reporters contain eight copies of the binding site for the lexA DNA binding protein inserted into the basal GAL1 promoter. The bioassay is diagrammed in FIG. 1. The tripartite fusion is able to activate transcription of the reporters in the presence of androgen hormone.

Example 2

Sensitivity to Testosterone

Figure 3:
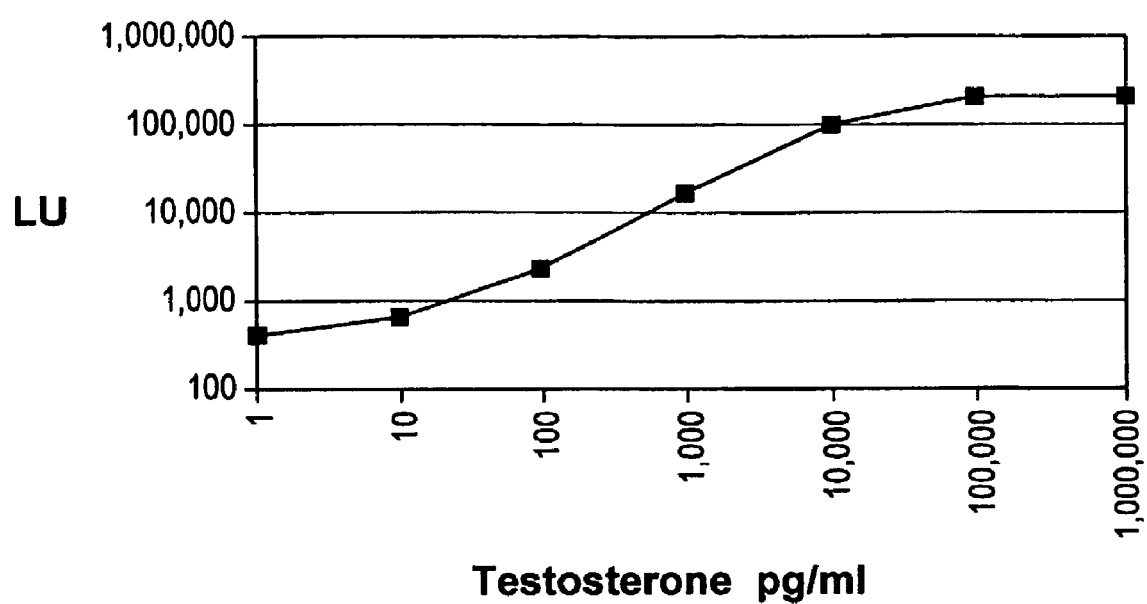
FIG. 3 illustrates the biosensitivity of a tripartite system to various concentrations of testosterone according to an embodiment of the present invention.
Figure 4:
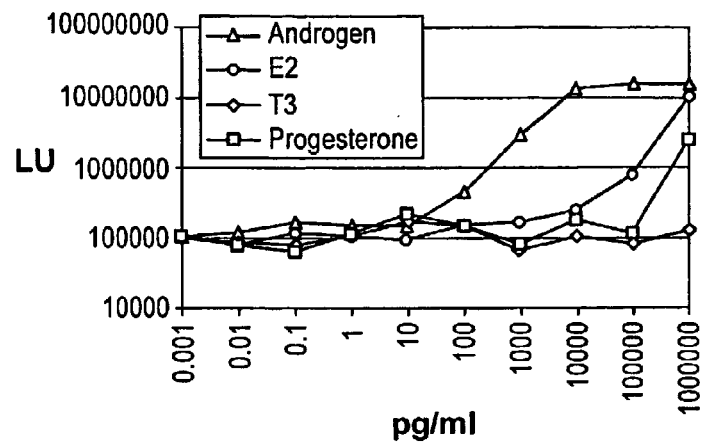
FIGS. 4A-4C illustrate bioselectivity of tripartite systems according to embodiments of the present invention.
Figure 4:
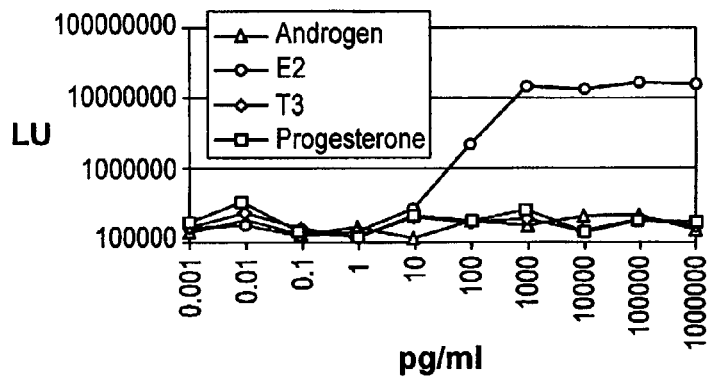
Figure 4:
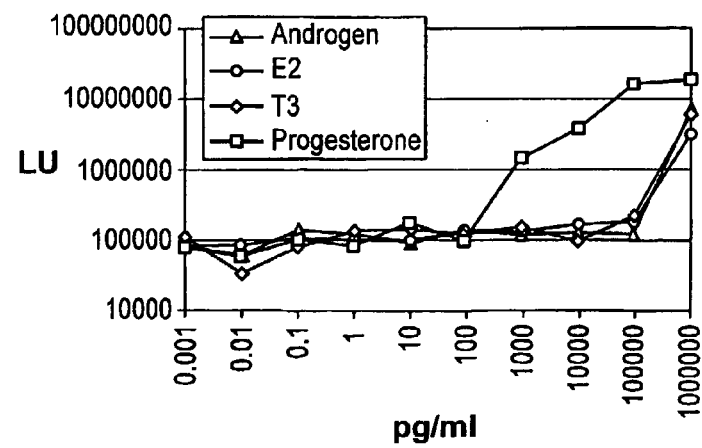

The sensitivity of the bioassay to testosterone was tested (FIGS. 3 and 4A). Various concentrations of testosterone were added to PBS/BSA and incubated with yeast harboring the tripartite receptor system. As shown in FIGS. 3 and 4A, a concentration of 100 pg/ml was capable of detection. The dynamic range extended over several logs of luciferase units. The range between 100 pg/ml and 100,000 pg/ml for testosterone yielded the most linear response. For comparison, testosterone in men is typically about 4-8 ng/ml (4,000-8,000 pg/ml), while in women it is about 0.1-0.54 ng/ml (~100 pg/mL-500 pg/mL) or less.

Example 3

Cross Reactivity

Hormone receptor structures are conserved. To determine if other steroids could cross-react with a specific receptor ligand-binding domain, three tripartite systems were studied in the presence of androgen, estrogen, testosterone and progesterone, wherein each of the systems contained a different hormone receptor ligand binding domain (e.g., AR-LBD, ER-LBD, and PR-LBD). As shown in FIG. 4A, only non-physiological concentrations of estrogen were able to activate the reporter. Estrogen and progesterone tripartite systems were also tested. As shown in FIGS. 4B and 4C, each bioassay shows specificity, responding only to its specific ligand.

Example 4

Detection of Anabolic Steroids

Figure 5:
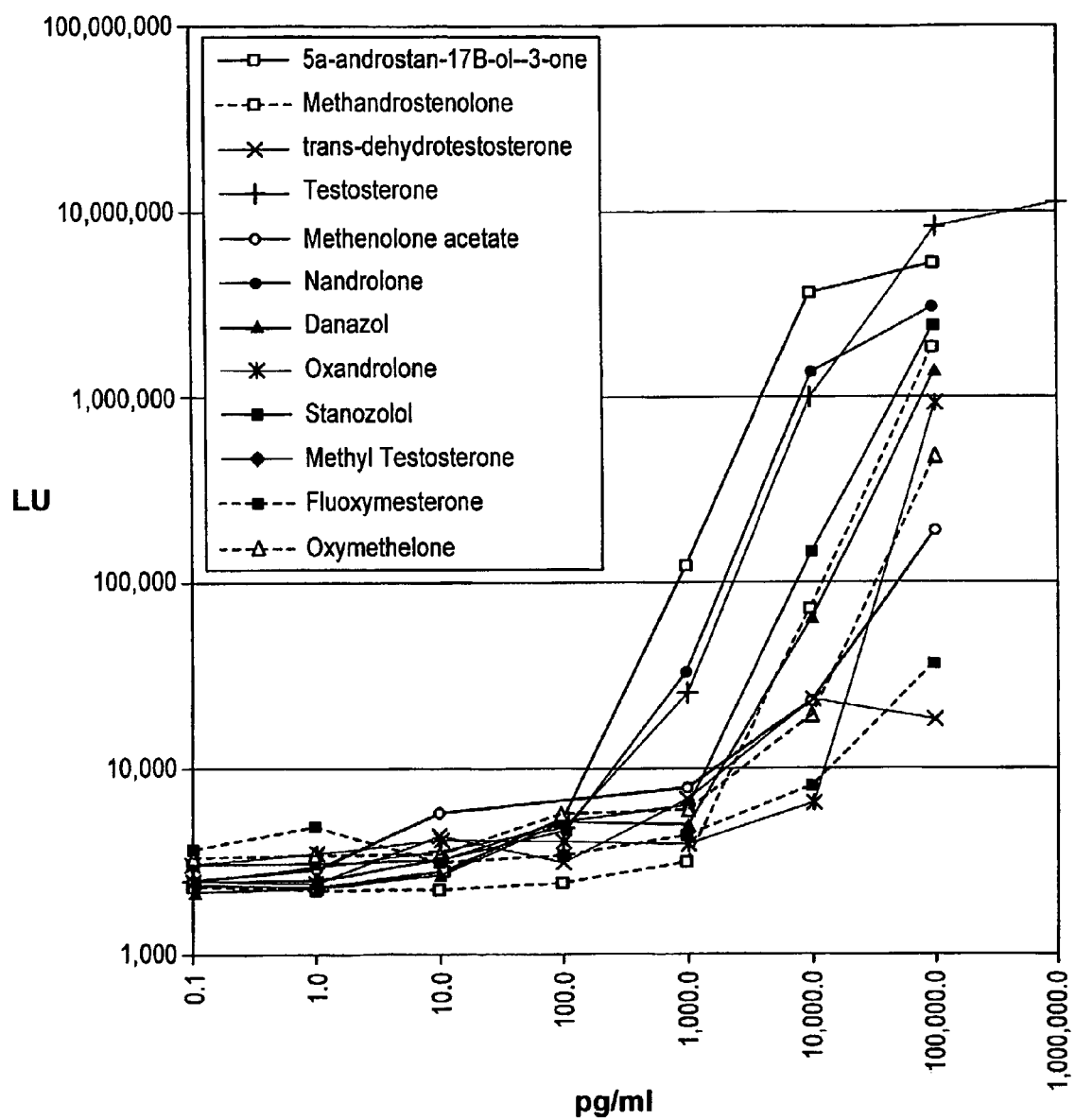
FIG. 5 illustrates a bioassay response of a tripartite system to testosterone derivatives according to an embodiment of the present invention.
Figure 6:
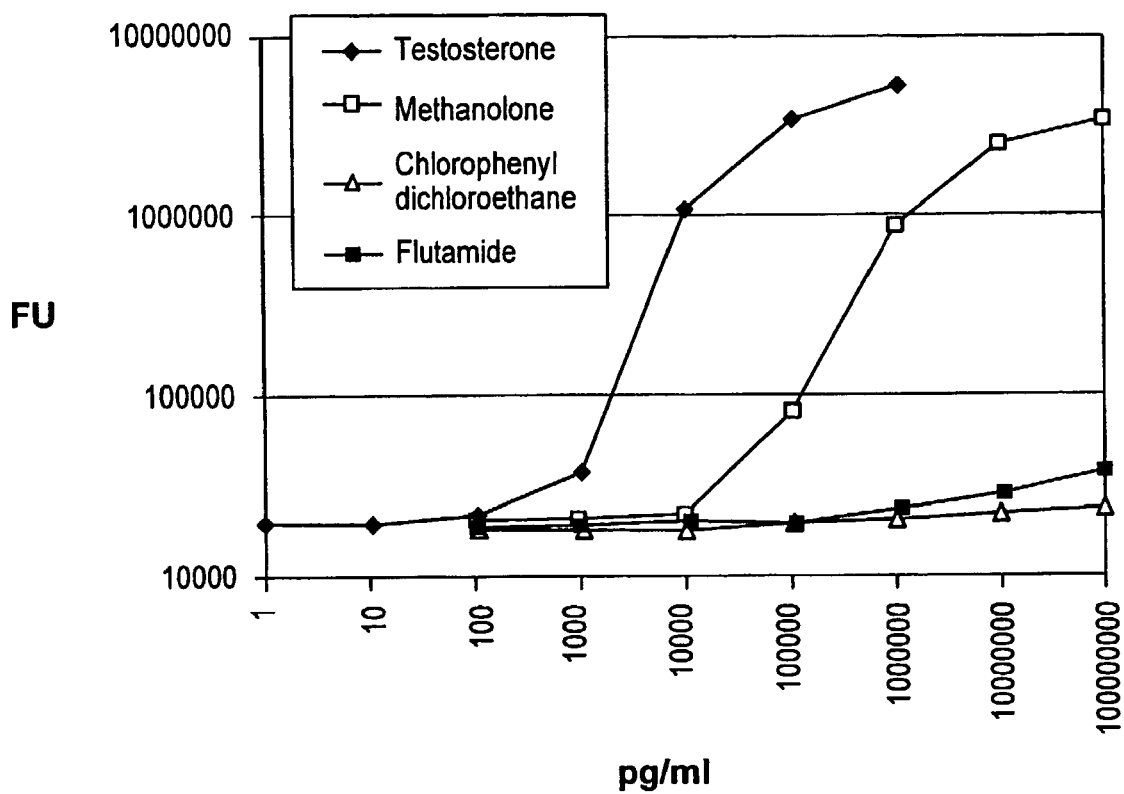
FIG. 6 illustrates a bioassay response of a tripartite system to testosterone inhibitors according to an embodiment of the present invention.

To determine if the androgen tripartite system could detect androgen derivatives, dilutions of several different anabolic steroids were prepared and their induction potentials determined. All of the androgens tested induced expression of the reporter construct (see FIG. 5). Consistent with the literature, DHT was the strongest of those tested. As shown in FIG. 6, the bioassay failed to detect flutamide and 1-(2-chlorophenyl)-1-(4-chlorophenyl)-2,2,-dichloroethane, which are both anti-androgens, indicating the particular androgen binding domain utilized does not bind androgen inhibitors or, if it does, binding does not result in activation or expression of the reporter construct. In body fluids samples with high bioactivity using the androgen bioassay and a lower value for testosterone by RIA or Mass Spectrometry; this would suggest a high concentration of a compound with high androgen action that is not testosterone. The same concept for progesterone and estrogen receptors apply, respectively.

Example 5

Comparison of ECI and Bioassay

Figure 7:
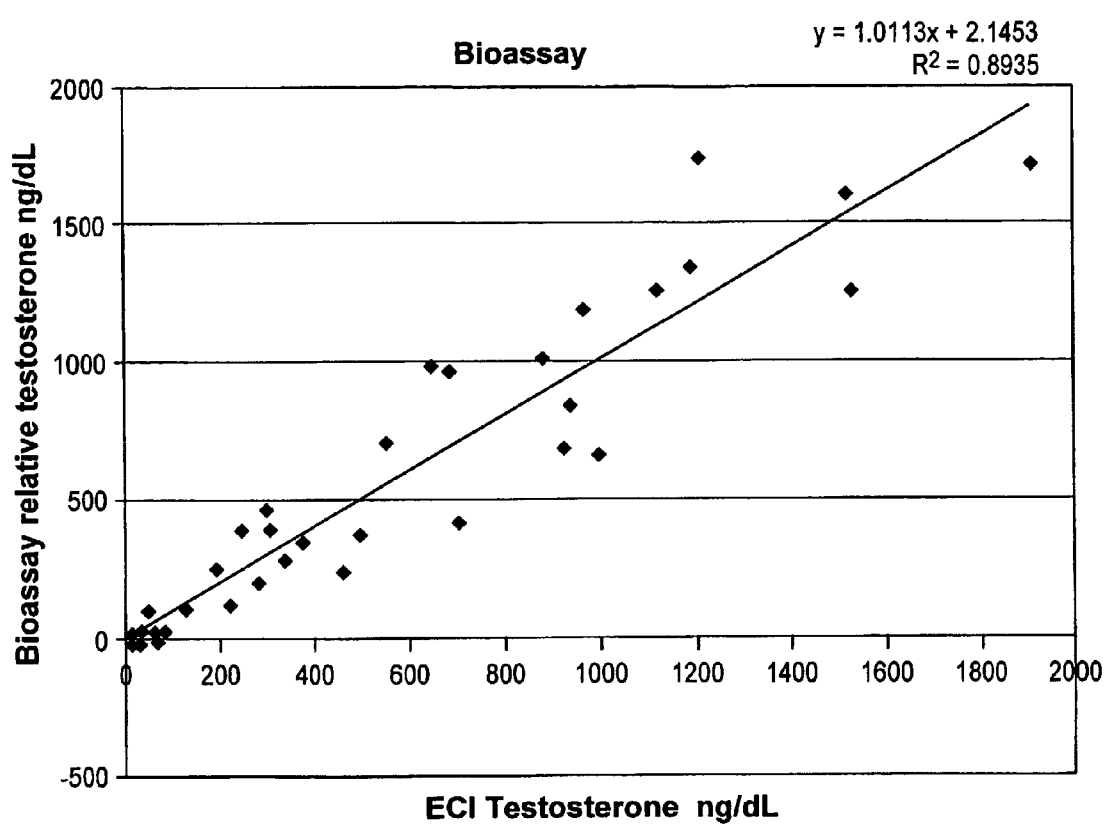
FIG. 7 illustrates a comparison of ECI and bioassay results according to an embodiment of the present invention.

To determine if there was a correlation between the yeast bioassay of the present invention and testosterone ECI values, serum samples from thirty-six individuals were processed that had ECI values ranging from 18-1910 ng/dL. As shown in FIG. 7, there was a strong correlation between bioactivity and ECI values (R=0.94, n=36). In addition, the result suggests that some of the bioactivity from the sample set tested may be attributed to testosterone.

Example 6

Activation of the Androgen Receptor by Progestin Derivatives

Elevated levels of androgen activity were found in sera from females using some formulations of birth control. The ability of medroxyprogesterone, ethynodial diacetate, 19-Norethindrone, 19-Norethindrone acetate, and levonorgestrel to induce transcription of the reporter through the androgen receptor tripartite were tested using the methods described above. Several progestins activated the androgen bioassay. Furthermore, the levonorgestrel (−/−) form had about a two-fold greater androgenic activity than the levonorgestrel (−/+) form (data not shown).

Example 7

Detection of Androgens and Progestins from Serum

Serum samples were pre-treated by diluting with an equal volume of 0.9 mg/mL K$_2$EDTA, (150 µl of serum was added to 150 µl of 0.9 mg/mL K$_2$ EDTA), vortexed briefly and heated for 5 min at 72 C. Pre-treated serum was added to yeast expressing the androgen or progesterone tripartite, prepared as follows.

Yeast were inoculated from a frozen stock into synthetic media lacking leucine, uracil, and histidine supplemented with 2% dextrose. After overnight incubation at 30° C., mid-log (OD600 nm 0.4-0.8) cells were washed with synthetic media lacking leucine, uracil, and histidine supplemented with glycerol and resuspended in 2% glycerol media at an absorbance at 600 nm of 0.1. Twenty-five microliters of mid-log yeast were added to each well of a 384-well plate using a, BioMek 2000 (Beckman-Coulter). Serum samples were diluted with an equal volume of 0.9 mg/mL K$_2$EDTA, (150 µL of serum was added to 150 µL of 0.9 mg/mL K$_2$ EDTA), vortexed briefly and heated for 5 min at 72° C. Ten microliters of pre-treated sample was added to the plate. Ten microliters of serially diluted compound in H$_2$O was incubated with 25 µL of yeast (Thermolabsystems). The plate was covered with Aeroseal sealing film (Research Products International, Palatine Ill.), and placed on a plate shaker for 5 min and the plate was incubated for 17-18 hr at 28° C. in a humidified incubator. After overnight incubation, the plate was shaken for 5 min. To detect β-galactosidase activity, 25 µL of Beta-Glo (Promega) was added to the cells incubated overnight using luminskan dispenser (Fisher Scientific). After about 2-hr incubation at room temperature, the β-galactosidase in the reaction mixture was determined using Luminskan luminometer (Thermolabsystems). Intra-assay variation is ~6.0%.

Figure 8:
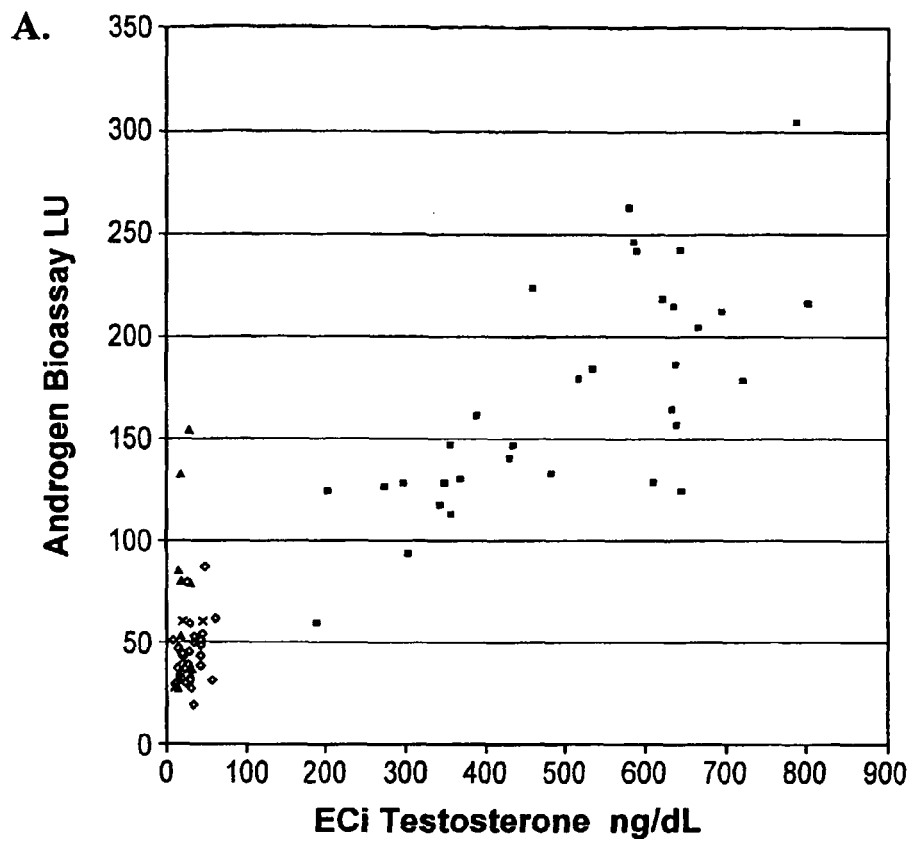
FIG. 8 illustrates the correlation between serum testosterone concentrations measured by both ECI and bioassay.
Figure 8:
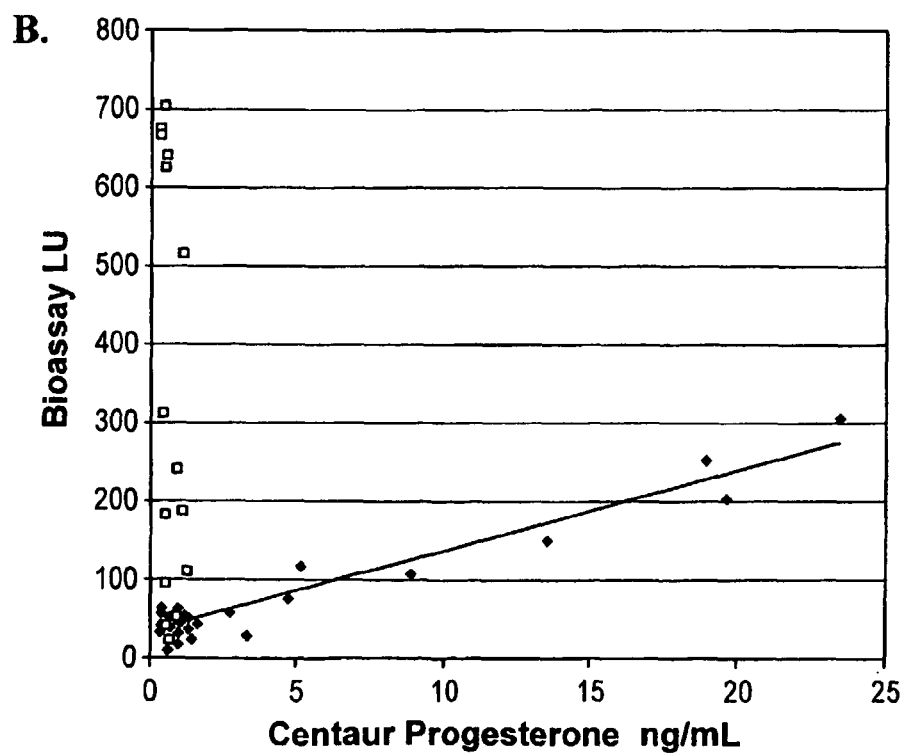

The results indicate that there is a strong correlation, $R_2 = 0.8576$ between serum testosterone concentrations measured by both ECI and bioactivity using the androgen assay with the exception of some women on birth control, see FIG. 8. The progesterone assay also showed a good correlation, $R_2 = 0.9197$, between progesterone values measured by the Centaur assay (Bayer HealthCare AG, Diagnostics Division, Tarrytown, N.Y.) and progesterone tripartite system for normal individuals not taking birth control. Females on some formulations of birth control pills, i.e. levonorgestrel, showed elevated androgen levels compared to untreated women. An increase was also observed with extracted samples. However, women on fourth generation progestin, i.e. drospireone, in general had lower androgen and progesterone levels. Drospireone is structurally related to spironolactone an androgen receptor inhibitor.

All of the COMPOSITIONS, METHODS and APPARATUS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS, METHODS and APPARATUS and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

TABLE 1

Plasmids used herein.

| Plasmid | Markers | Reference |
|---|---|---|
| LexA:ER:VP16 | pADH-LexA-DBD:ER-LBD:VP16, 2u, Amp | Balasubramanian and Morse, 1999 |
| pRS413-GPD | pGPD, HIS, CEN, Amp | Mumberg et al., 1995 |
| pARUP21 | pGPD-LexA-DBD:ER-LBD:VP16, HIS, CEN, Amp | Used herein |
| pARUP27 | pGPD-LexA-DBD:AR_LBD:VP16, HIS, CEN, Amp | Used herein |
| pARUP32 | pGPD-LexA-DBD:PR-LBD:VP16, HIS, CEN, Amp | Used herein |

TABLE 2

Yeast strains used herein.

| Strain | Markers | Reference |
|---|---|---|
| DY151 | MATα ade2-1 can1-100 his3-11, 15 leu2-3, 112 trp1-1 ura3-1 | Stillman |
| DY6877 | MATa ade2-1 can1-100 his3-11, 15 leu2-3, 112 trp1-1 ura3-1 lys2Δ25 URA3::Lex8op-lacZ | Stillman |
| yARUP3 | MATα ade2-1 can1-100 his3-11, 15 leu2-3, 112 trp1-1 ura3-1 LEU2::Lex8op-Luciferase | Used herein |
| yARUP16 | yARUP16 MATa/MATα ade2-1/ade2-1 can1-100/can1-100 his3-11, 15/his3-11, 15 trp1-1/trp1-1 ura3-1/URA3::Lex8op-lacZ, leu2-3, 112/LEU2::Lex8op-Luciferase | Used herein |
| yARUP23 | yARUP16 MATa/MATα ade2-1/ade2-1 can1-100/can1-100 his3-11, 15/his3-11, 15 trp1-1/trp1-1 ura3-1/URA3::Lex8op-lacZ, leu2-3, 112/LEU2::Lex8op-Luciferase pARUP21 [pGPD-LexA-DBD:ER-LBD:VP16] | Used herein |
| yARUP45 | yARUP16 MATa/MATα ade2-1/ade2-1 can1-100/can1-100 his3-11, 15/his3-11, 15 trp1-1/trp1-1 ura3-1/URA3::Lex8op-lacZ, leu2-3, 112/LEU2::Lex8op-Luciferase pARUP27 [pGPD-LexA-DBD:AR-LBD:VP16] | Used herein |
| yARUP49 | yARUP16 MATa/MATα ade2-1/ade2-1 can1-100/can1-100 his3-11, 15/his3-11, 15 trp1-1/trp1-1 ura3-1/URA3::Lex8op-lacZ, leu2-3/LEU2::Lex8op-Luciferase pARUP32 [pGPD-LexA-DBD:PR-LBD:VP16] | Used herein |

All strains are isogenic, differing from each other in only the markers and/or plasmid indicated. They are all derived from W303, Thomas, B. J. and R. Rothstein. 1989 Elevated recombination rates in transcriptionally active DNA. *Cell.* 56: 619-630.

REFERENCES

BALASUBRAMANIAN, B., and R. H. MORSE, 1999 Binding of Gal4p and biocoid to nucleosomal sites in yeast in the absence of replication. Mol. Cell Biol. 19: 2977-2985.

BECK, V., E. UNTERRIEDER, L. KRENN, W. KUBELKA, and A. JUNGBAUER, 2003 Comparison of hormonal activity (estrogen, androgen and progestin) of standardized plant extracts for large scale use in hormone replacement therapy. J. Steroid Biochem. Mol. Biol. 84: 259-268.

BERGHOFER-HOCHHEINER, Y., C. ZUREK, G. LANGER and T. MUNDER, 1997 Expression of the vitamin D and the retinoid X receptors in *Saccharomyces cerevisiae*: alternative in vivo models for ligand-induced transactivation. J. Cell Biochem. 66: 184-196.

DORFMAN, R. and R. SHIPLEY, 1956 Androgens. John Wiley and Sons, Inc. Chapman and Hall, Limited.

EVANS, R. M., 1988 The steroid and thyroid hormone receptor superfamily. Science 240: 889-895.

EVANS, R. M. and C. J. DON, Apr. 22, 2003 Transcriptional co-repressor that interacts with nuclear hormone receptors and uses therefor.

EVANS, R. M., D. J. MANGELSDORF, E. S. ONG, A. E. ORO, U. K. BORGMEYER et al., Dec. 9, 1997 Orphan steroid hormone receptors. 463694. U.S. Pat. No. 5,696,233.

EVANS, R. M., D. J. MANGELSDORF, E. S. ONG, A. E. ORO, U. K. BORGMEYER et al., Jan. 20, 1998 Methods of using novel steroid hormone orphan receptors. 694501. U.S. Pat. No. 5,700,004.

EVANS, R. M. and L. NAGY, May 14, 2002 Compounds useful for the modulation of processes mediated by nuclear hormone receptors, methods for the identification and use of such compounds. 846881. U.S. patent GAIDO, K. W., L. S. LEONARD, S. LOVELL, J. C. GOULD, D. BABAI et al., 1997 Evaluation of chemicals with endocrine modulating activity in a yeast-based steroid hormone receptor gene transcription assay. Toxicol. Appl. Pharmacol. 143: 205-212.

GAO, C. Y. and J. L. PINKHAM, 2000 Tightly regulated, beta-estradiol does-dependent expression system for yeast. Biotechniques 29: 1226-1231.

GONG, Y., H. S. CHIN, L. S. LIM, C. J. LOY, J. P. OBBARD et al., 2003 Clustering of sex hormone disruptors in Singapore's marine environment. Environ. Health Perspect. 111: 1448-1453.

JIN, C. H. and J. W. PIKE, 1996 Human vitamin D receptor-dependent transactivation in *Saccharomyces cerevisiae* requires retinoid X receptor. Mol. Endocrinol. 10: 196-205.

KLIEN, K. O., J. BARON, K. M. BARNES, O. H. PESCOVITZ and G. B. CUTLER, JR., 1998 Use of an ultrasensitive recombinant cell bioassay to determine estrogen levels in girls with precocious puberty treated with a luteinizing hormone-releasing hormone agonist. J. Clin. Endocrinol. Metab. 83: 2387-2389.

KLIEN, K. O., J. BARON, M. J. COLLI, D. P. MCDONNELL and G. B. CUTLER, JR., 1994 Estrogen levels in childhood determined by an ultrasensitive recombinant cell bioassay. J. Clin. Invest. 94: 2475-2480.

KLIEN, K. O., L. M. DEMERS, S. J. SANTBER, J. BARON, G. B. CUTLER, J R. et al., 1995 Use of ultrasensitive recombinant cell bioassay to measure estrogen levels in women with breast cancer receiving the aromatase inhibitor, letrozole. J. Clin. Endocrinol. Metab. 80: 2658-2660.

KLIEN, K. O., V. MERICQ, J. M. BROWN-DAWSON, K. A. LARMORE, P. CABEZAS et al., 1999 Estrogen levels in girls with premature thelarche compared with normal prepubertal girls as determined by an ultrasensitive recombinant cell bioassay. J. Pediatr. 134: 190-192.

KUHN, C. M., 2002 Anabolic steroids. Recent Prog. Horm. Res. 57: 411-434.

LARMORE K. A. and K. O. KLIEN, 2000 Estradiol suppression and recovery during leuprolide acetate treatment in women as determined weekly by an ultrasensitive recombinant cell bioassay. Gynecol. Endocrinol. 14: 405-410.

LEE, H. J., Y. S. LEE, H. B. KWON and K. LEE, 2003 Novel yeast bioassay system for detection of androgenic and anti-androgenic compounds. Toxicol. In Vitro 17: 237-244.

LOUVION, J. F., B. HAVAUX-COPF and D. PICARD, 1993 Fusion of GAL4-VP16 to a steroid-binding domain provides a tool for gratuitous induction of galactose-responsive genes in yeast. Gene 131: 129-134.

MAURAS, N., K. O. O'BRIEN, K. O. KLIEN and V. HAYES, 2000 Estrogen suppression in males: metabolic effects. J. Clin. Endocrinol. Metab. 85: 2370-2377.

MCKENNAN, N. J., R. B. LANZ, and B. W. O'MALLEY, 1999 Nuclear receptor coregulators: cellular and molecular biology. Endocr. Rev. 20: 321-344.

MEIKLE, W., 2003 Androgen replacement therapy of male hypogonadism, pp. 333-368 in Endocrine Replacement Therapy in Clinical Practice, edited by W. MEIKLE. Humana Press.

MUMBERG, D., R. MULLER and M. FUNK, 1994 Regulatable promoters of *Saccharomyces cerevisiae*: comparison of transcriptional activity and their use for heterologous expression. Nucleic Acids Res. 22: 5767-5768.

MUMBERG, D., R. MULLER and M. FUNK, 1995 Yeast vectors for the controlled expression of heterologous proteins in different genetic backgrounds. Gene 156: 119-122.

PAJIC, T., M. VITAS, D. ZIGON, A. PAVKO, S. L. KELLY et al., 1999 Biotransformation of steroids by the fission yeast *Schizosaccharomyces pombe*. Yeast 15: 639-645.

PARIS, F. N. SERVANT, B. TEROUANNE, P. BALAGUER, J. C. NICOLAS et al., 2002 A new Recombinant cell bioassay for ultrasensitive determination of serum estrogenic bioactivity in children. J. Clin. Endocrinol. Metab. 87: 791-797.

RONICKE, V., W. GRAULICH, D. MUMBERG, R. MULLER, and M. FUNK, 1997 Use of conditional promoters for expression of heterologous proteins in *Saccharomyces cerevisiae*. Methods Enzymol. 283: 313-322.

SAYLER, G. S., M. L. SIMPSON, B. M. APPLEGATE and R. S. A., Jan. 6, 2004 In vivo biosensor apparatus and method of use. 454071. U.S. patent SHIRAISHI, F., T. OKUMURA, M. NOMACHI, S. SERIZAWA, J. NISHIKAWA et al., 2003 Estrogenic and thyroid hormone activity of a series of hydroxyl-polychlorinated biphenyls. Chemosphere 52: 3342.

SOTO, A. M., C. SONNENSCHEIN, K. L. CHUNG, M. F. FERNANDEZ, N. OLEA et al., 1995 The E-SCREEN assay as a tool to identify estrogens: an update on estrogenic environmental pollutants. Environ. Health Perspect. 103 Suppl 7: 113-122.

TRAN, H. T., S. SHAABAN, H. ASKARI, M. SCHWARTZ and T. BUTT, Nov. 13, 2003 Methods and Compositions for Identifying Ligands for Nuclear Receptors. 10/204, 169. United States patent application.

WALFISH, P. G., T. YAGANATHAN, Y. F. YANG, H. HONG, T. R. BUTT et al., 1997 Yeast hormone response element assays detect and characterize GRIP1 coactivator-dependent activation of transcription by thyroid and retinoid nuclear receptors. Proc. Natl. Acad. Sci. USA 94: 3697-3702.

WANG, Y., B. W. O'MALLEY, JR., S. Y. TSAI and B. W. O'MALLEY, 1994 A regulatory system for use in gene transfer. Proc. Natl. Acad. Sci. USA 91: 8180-8184.

WEINSTEIN, B., L. H. KELLER and S. R. PALLI, Jun. 10, 2003 Method for identifying products employing gene expression. 690391. U.S. Pat. No. 6,576,422.

We claim:

1. A method for detecting steroids comprising the steps of:
   (a) providing a host cell transformed with a reporter gene and a tripartite construct, said tripartite construct encoding a ligand binding domain (LBD) wherein said LBD is selected from the group consisting of SEQ ID NO:3, SEQ ID NO:5, and SEQ ID NO:7, operably linked to both a DNA binding domain (DBD) comprising SEQ ID NO:1 and an activation domain (AD) comprising SEQ ID NO:9, wherein said host cell expresses said reporter gene upon binding of the LBD to generate a detectable signal;
   (b) contacting said host cell with a mammalian sample to be screened for a compound that binds to said LBD, wherein the contacting is in vitro; and
   (c) detecting the presence of the signal generated by expression of said reporter gene in order to detect the amount of steroids present in the sample.

2. The method of claim 1, wherein said host cell is a yeast cell or a modified yeast cell.

3. The method of claim 2, wherein said yeast cell or modified yeast cell is *Saccharomyces cerevisiae.*

4. The method of claim 1, wherein said reporter gene is selected from the group consisting of β-galactosidase, green fluorescent protein, luciferase, β-glucuronidase, chloramphenicol acetyltransferase, and alkaline phosphatase.

5. A method for determining the steroid activity of a mammalian sample, said method comprising the steps of:
   (a) contacting the mammalian sample with a cell comprising:
      (i) a reporter plasmid; and
      (ii) a fusion protein comprising a ligand-binding domain (LBD), wherein the LBD is selected from the group consisting of SEQ ID NO:4, SEQ ID NO:6, and SEQ ID NO:8, operably linked to both a DNA binding domain (DBD) comprising SEQ ID NO:2 and an activation domain (AD) comprising SEQ ID NO:10, where said fusion protein binds to binding sites in said reporter plasmid, wherein the contacting is in vitro;
   (b) allowing the sample to incubate with said cell;
   (c) measuring the reporter activity of said cell;
   (d) comparing the measured reporter activity to an amount of reporter activity, observed when known quantities of a steroid are contacted with said cell, to give a relative reporter activity of the sample, and
   (e) using the relative reporter activity to detect or quantify an active steroid in the sample.

6. The method according to claim 5, wherein the mammalian sample is selected from the group consisting of a serum sample, a plasma sample and a urine sample.

7. The method of claim 5, wherein said reporter gene is selected from the group consisting of β-galactosidase, green fluorescent protein, luciferase, 13-glucuronidase, chloramphenicol acetyltransferase, and alkalinephosphatase.

8. A tripartite construct comprising:
   (a) a DNA binding domain comprising SEQ ID NO:1;
   (b) a ligand binding domain selected from the group consisting of SEQ ID NO:3, SEQ ID NO:5, and SEQ ID NO:7; and
   (c) an activation domain comprising SEQ ID NO:9.

9. A plasmid comprising a tripartite construct comprising:
(a) a DNA binding domain comprising SEQ ID NO:1;
(b) a ligand binding domain selected from the group consisting of SEQ ID NO:3 SEQ ID NO:5, and SEQ ID NO:7; and
(c) an activation domain comprising SEQ ID NO:9.

10. An isolated host cell comprising a plasmid comprising:
(a) a DNA binding domain comprising SEQ ID NO: 1;
(b) a ligand binding domain selected from the group consisting of SEQ ID NO:3, SEQ ID NO:5, and SEQ ID NO:7; and
(c) an activation domain comprising SEQ ID NO:9
wherein said host cell further comprises DNA that transcribes a reporter gene when associated with an activated form of said tripartite construct.

11. The host cell of claim 10, wherein said reporter gene is selected from the group consisting of β-galactosidase, green fluorescent protein, luciferase, β-glucuronidase, chloramphenicol acetyltransferase, and alkaline phosphatase.

12. A kit for detecting steroidal activity of a sample, said kit comprising:
(a) host cells comprising a plasmid comprising
  (i) a DNA binding domain comprising SEQ ID NO:1;
  (ii) a ligand binding domain selected from the group consisting of SEQ ID NO:3, SEQ ID NO:5, and SEQ ID NO:7; and
  (iii) an activation domain comprising SEQ ID NO:9; and
(b) instructions for detecting said steroidal activity.

\* \* \* \* \*

SEQUENCE LISTING

<160> NUMBER OF SEQ ID NOS: 14

<210> SEQ ID NO 1
<211> LENGTH: 625
<212> TYPE: DNA
<213> ORGANISM: Escherichia coli

<400> SEQUENCE: 1

```
atgaaagcgt taacggccag gcaacaagag gtgtttgatc tcatccgtga tcacatcagc      60
cagacaggta tgccgccgac gcgtgcggaa atcgcgcagc gtttggggtt ccgttcccca     120
aacgcggctg aagaacatct gaaggcgctg gcacgcaaag gcgttattga aattgtttcc     180
ggcgcatcac gcgggattcg tctgttgcag gaagaggaag aagggttgcc gctggtaggt     240
cgtgtggctg ccggtgaacc acttctggcg caacagcata ttgaaggtca ttatcaggtc     300
gatccttcct tattcaagcc gaatgctgat ttcctgctgc gcgtcagcgg gatgtcgatg     360
aaagatatcg gcattatgga tggtgacttg ctggcagtgc ataaaactca ggatgtacgt     420
aacggtcagg tcgttgtcgc acgtattgat gacgaggtta ccgttaagcg cctgaaaaaa     480
cagggcaata agtcgaact gttgccagaa aatagcgagt ttaaaccaat tgtcgtagat      540
cttcgtcagc agagcttcac cattgaaggg ctggcggttg gggttattcg caacggcgac     600
tggctggaat tcccggggat cccac                                           625
```

<210> SEQ ID NO 2
<211> LENGTH: 208
<212> TYPE: PRT
<213> ORGANISM: Escherichia coli

<400> SEQUENCE: 2

```
Met Lys Ala Leu Thr Ala Arg Gln Gln Glu Val Phe Asp Leu Ile Arg
1               5                  10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro Leu Leu Ala Gln Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu Glu Phe Pro Gly Ile Pro
        195                 200                 205
```

<210> SEQ ID NO 3
<211> LENGTH: 932
<212> TYPE: DNA
<213> ORGANISM: Human

<400> SEQUENCE: 3

```
gggatcccac ctatcgatat cagtcgagct tctgctggag acatgagagc tgccaacctt      60
tggccaagcc cgctcatgat caaacgctct aagaagaaca gcctggcctt gtccctgacg     120
gccgaccaga tggtcagtgc cttgttggat gctgagcccc ccatactcta ttccgagtat     180
gatcctacca gacccttcag tgaagcttcg atgatgggct tactgaccaa cctggcagac     240
agggagctgg ttcacatgat caactgggcg aagagggtgc caggctttgt ggatttgacc     300
ctccatgatc aggtccacct tctagaatgt gcctggctag agatcctgat gattggtctc     360
gtctggcgct ccatggagca cccagtgaag ctactgtttg ctcctaactt gctcttggac     420
aggaaccagg gaaaatgtgt agagggcatg gtggagatct tcgacatgct gctggctaca     480
tcatctcggt tccgcatgat gaatctgcag ggagaggagt ttgtgtgcct caaatctatt     540
attttgctta attctggagt gtacacattt ctgtccagca ccctgaagtc tctggaagag     600
aaggaccata tccaccgagt cctggacaag atcacagaca ctttgatcca cctgatggcc     660
aaggcaggcc tgaccctgca gcagcagcac cagcggctgg cccagctcct cctcatcctc     720
tcccacatca ggcacatgag taacaaaggc atggagcatc tgtacagcat gaagtgcaag     780
aacgtggtgc cctctatga cctgctgctg gagatgctgg acgccaccg cctacatgcg      840
cccactagcc gtggaggggc atccgtggag gagacggacc aaagccactt ggccactgcg     900
ggctctactt catcgatgat cacggcgtcg ac                                   932
```

<210> SEQ ID NO 4
<211> LENGTH: 310
<212> TYPE: PRT
<213> ORGANISM: Human

<400> SEQUENCE: 4

```
Gly Ile Pro Pro Ile Asp Ile Ser Arg Ala Ser Ala Gly Asp Met Arg
1               5                   10                  15

Ala Ala Asn Leu Trp Pro Ser Pro Leu Met Ile Lys Arg Ser Lys Lys
            20                  25                  30

Asn Ser Leu Ala Leu Ser Leu Thr Ala Asp Gln Met Val Ser Ala Leu
        35                  40                  45

Leu Asp Ala Glu Pro Pro Ile Leu Tyr Ser Glu Tyr Asp Pro Thr Arg
    50                  55                  60

Pro Phe Ser Glu Ala Ser Met Met Gly Leu Leu Thr Asn Leu Ala Asp
65                  70                  75                  80

Arg Glu Leu Val His Met Ile Asn Trp Ala Lys Arg Val Pro Gly Phe
                85                  90                  95

Val Asp Leu Thr Leu His Asp Gln Val His Leu Leu Glu Cys Ala Trp
            100                 105                 110

Leu Glu Ile Leu Met Ile Gly Leu Val Trp Arg Ser Met Glu His Pro
        115                 120                 125

Val Lys Leu Leu Phe Ala Pro Asn Leu Leu Asp Arg Asn Gln Gly
    130                 135                 140

Lys Cys Val Glu Gly Met Val Glu Ile Phe Asp Met Leu Leu Ala Thr
145                 150                 155                 160

Ser Ser Arg Phe Arg Met Met Asn Leu Gln Gly Glu Glu Phe Val Cys
```

```
                    165                 170                 175
Leu Lys Ser Ile Ile Leu Leu Asn Ser Gly Val Tyr Thr Phe Leu Ser
            180                 185                 190

Ser Thr Leu Lys Ser Leu Glu Glu Lys Asp His Ile His Arg Val Leu
        195                 200                 205

Asp Lys Ile Thr Asp Thr Leu Ile His Leu Met Ala Lys Ala Gly Leu
    210                 215                 220

Thr Leu Gln Gln Gln His Gln Arg Leu Ala Gln Leu Leu Leu Ile Leu
225                 230                 235                 240

Ser His Ile Arg His Met Ser Asn Lys Gly Met Glu His Leu Tyr Ser
            245                 250                 255

Met Lys Cys Lys Asn Val Val Pro Leu Tyr Asp Leu Leu Leu Glu Met
        260                 265                 270

Leu Asp Ala His Arg Leu His Ala Pro Thr Ser Arg Gly Gly Ala Ser
    275                 280                 285

Val Glu Glu Thr Asp Gln Ser His Leu Ala Thr Ala Gly Ser Thr Ser
    290                 295                 300

Ser Met Ile Thr Ala Ser
305                 310

<210> SEQ ID NO 5
<211> LENGTH: 766
<212> TYPE: DNA
<213> ORGANISM: Human

<400> SEQUENCE: 5
ggatcccatg tcagcccatc tttctgaatg tcctggaagc cattgagcca ggtgtagtgt     60
gtgctggaca cgacaacaac cagcccgact cctttgcagc cttgctctct agcctcaatg    120
aactgggaga gagacagctt gtacacgtgg tcaagtgggc caaggccttg cctggcttcc    180
gcaacttaca cgtggacgac cagatggctg tcattcagta ctcctggatg gggctcatgg    240
tgtttgccat gggctggcga tccttcacca atgtcaactc caggatgctc tacttcgccc    300
ctgatctggt tttcaatgag taccgcatgc acaagtcccg gatgtacagc cagtgtgtcc    360
gaatgaggca cctctctcaa gagtttggat ggctccaaat cacccccag gaattcctgt     420 gcatgaaagc actgctactc ttcagcatta ttccagtgga tgggctgaaa atcaaaaat    480 tctttgatga acttcgaatg aactacatca aggaactcga tcgtatcatt gcatgcaaaa    540
gaaaaaatcc cacatcctgc tcaagacgct ctaccagct caccaagctc ctggactccg    600
tgcagcctat tgcgagagag ctgcatcagt tcactttga cctgctaatc aagtcacaca    660
tggtgagcgt ggactttccg gaaatgatgg cagagatcat ctctgtgcaa gtgcccaaga    720
tcctttctgg gaaagtcaag cccatctatt ccacaccgc gtcgac                   766

<210> SEQ ID NO 6
<211> LENGTH: 255
<212> TYPE: PRT
<213> ORGANISM: Human

<400> SEQUENCE: 6

Gly Ile Pro Cys Gln Pro Ile Phe Leu Asn Val Leu Glu Ala Ile Glu
1               5                   10                  15

Pro Gly Val Val Cys Ala Gly His Asp Asn Asn Gln Pro Asp Ser Phe
            20                  25                  30

Ala Ala Leu Leu Ser Ser Leu Asn Glu Leu Gly Glu Arg Gln Leu Val
        35                  40                  45
```

```
His Val Val Lys Trp Ala Lys Ala Leu Pro Gly Phe Arg Asn Leu His
    50                  55                  60

Val Asp Asp Gln Met Ala Val Ile Gln Tyr Ser Trp Met Gly Leu Met
65                  70                  75                  80

Val Phe Ala Met Gly Trp Arg Ser Phe Thr Asn Val Asn Ser Arg Met
                85                  90                  95

Leu Tyr Phe Ala Pro Asp Leu Val Phe Asn Glu Tyr Arg Met His Lys
            100                 105                 110

Ser Arg Met Tyr Ser Gln Cys Val Arg Met Arg His Leu Ser Gln Glu
        115                 120                 125

Phe Gly Trp Leu Gln Ile Thr Pro Gln Glu Phe Leu Cys Met Lys Ala
    130                 135                 140

Leu Leu Leu Phe Ser Ile Ile Pro Val Asp Gly Leu Lys Asn Gln Lys
145                 150                 155                 160

Phe Phe Asp Glu Leu Arg Met Asn Tyr Ile Lys Glu Leu Asp Arg Ile
                165                 170                 175

Ile Ala Cys Lys Arg Lys Asn Pro Thr Ser Cys Ser Arg Arg Phe Tyr
            180                 185                 190

Gln Leu Thr Lys Leu Leu Asp Ser Val Gln Pro Ile Ala Arg Glu Leu
        195                 200                 205

His Gln Phe Thr Phe Asp Leu Leu Ile Lys Ser His Met Val Ser Val
    210                 215                 220

Asp Phe Pro Glu Met Met Ala Glu Ile Ile Ser Val Gln Val Pro Lys
225                 230                 235                 240

Ile Leu Ser Gly Lys Val Lys Pro Ile Tyr Phe His Thr Ala Ser
                245                 250                 255

<210> SEQ ID NO 7
<211> LENGTH: 565
<212> TYPE: DNA
<213> ORGANISM: Human

<400> SEQUENCE: 7
ggatcccaca gttgattcca ccactgatca acctgttaat gagcattgaa ccagatgtga    60
tctatgcagg acatgacaac acaaaacctg acacctccag ttctttgctg acaagtctta   120
atcaactagg cgagaggcaa cttctttcag tagtcaagtg gtctaaatca ttgccaggtt   180
ttcgaaactt acatattgat gaccagataa ctctcattca gtattcttgg atgagcttaa   240
tggtgtttgg tctaggatgg agatcctaca acatgtcag tgggcagatg ctgtattttg    300
cacctgatct aatactaaat gaacagcgga tgaaagaatc atcattctat tcattatgcc   360
ttaccatgtg gcagatccca caggagtttg tcaagcttca agttagccaa gaagagttcc   420
tctgtatgaa agtattgtta cttccttaata caattccttt ggaagggcta cgaagtcaaa   480
cccagtttga ggagatgagg tcaagctaca ttagagagct catcaaggca attggtttga   540
ggcaaaaagg agttgtgtcg agctc                                          565

<210> SEQ ID NO 8
<211> LENGTH: 256
<212> TYPE: PRT
<213> ORGANISM: Human

<400> SEQUENCE: 8

Gly Ile Pro Gln Leu Ile Pro Pro Leu Ile Asn Leu Leu Met Ser Ile
1               5                   10                  15

Glu Pro Asp Val Ile Tyr Ala Gly His Asp Asn Thr Lys Pro Asp Thr
            20                  25                  30
```

```
Ser Ser Ser Leu Leu Thr Ser Leu Asn Gln Leu Gly Glu Arg Gln Leu
         35                  40                  45

Leu Ser Val Val Lys Trp Ser Lys Ser Leu Pro Gly Phe Arg Asn Leu
 50                  55                  60

His Ile Asp Asp Gln Ile Thr Leu Ile Gln Tyr Ser Trp Met Ser Leu
 65                  70                  75                  80

Met Val Phe Gly Leu Gly Trp Arg Ser Tyr Lys His Val Ser Gly Gln
                 85                  90                  95

Met Leu Tyr Phe Ala Pro Asp Leu Ile Leu Asn Glu Gln Arg Met Lys
            100                 105                 110

Glu Ser Ser Phe Tyr Ser Leu Cys Leu Thr Met Trp Gln Ile Pro Gln
            115                 120                 125

Glu Phe Val Lys Leu Gln Val Ser Gln Glu Glu Phe Leu Cys Met Lys
            130                 135                 140

Val Leu Leu Leu Leu Asn Thr Ile Pro Leu Glu Gly Leu Arg Ser Gln
145                 150                 155                 160

Thr Gln Phe Glu Glu Met Arg Ser Ser Tyr Ile Arg Glu Leu Ile Lys
                165                 170                 175

Ala Ile Gly Leu Arg Gln Lys Gly Val Val Ser Ser Gln Arg Phe
            180                 185                 190

Tyr Gln Leu Thr Lys Leu Leu Asp Asn Leu His Asp Leu Val Lys Gln
            195                 200                 205

Leu His Leu Tyr Cys Leu Asn Thr Phe Ile Gln Ser Arg Ala Leu Ser
            210                 215                 220

Val Glu Phe Pro Glu Met Met Ser Glu Val Ile Ala Ala Gln Leu Pro
225                 230                 235                 240

Lys Ile Leu Ala Gly Met Val Lys Pro Leu Leu Phe His Lys Ala Ser
                245                 250                 255

<210> SEQ ID NO 9
<211> LENGTH: 226
<212> TYPE: DNA
<213> ORGANISM: Herpes Virus

<400> SEQUENCE: 9
gtcgaccgat gtcagcctgg gggacgagct ccacttagac ggcgaggacg tggccatggc      60
gcatgccgac gctctagacg atttcgatct ggacatgttg ggggacgggg attccccggg     120
tccgggattt acccccacg actccgcccc ctacggcgcc ctggatatgg ccgacttcga     180
attcgagcag atgtttaccg atgcccttgg aatttaggag ctcgag                    226

<210> SEQ ID NO 10
<211> LENGTH: 71
<212> TYPE: PRT
<213> ORGANISM: Herpes Virus

<400> SEQUENCE: 10

Ser Thr Asp Val Ser Leu Gly Asp Glu Leu His Leu Asp Gly Glu Asp
 1               5                  10                  15

Val Ala Met Ala His Ala Asp Ala Leu Asp Asp Phe Asp Leu Asp Met
                20                  25                  30

Leu Gly Asp Gly Asp Ser Pro Gly Pro Gly Phe Thr Pro His Asp Ser
            35                  40                  45

Ala Pro Tyr Gly Ala Leu Asp Met Ala Asp Phe Glu Phe Glu Gln Met
         50                  55                  60

Phe Thr Asp Ala Leu Gly Ile
                65
```

```
<210> SEQ ID NO 11
<211> LENGTH: 41
<212> TYPE: DNA
<213> ORGANISM: Primer

<400> SEQUENCE: 11
ggctgacatc ggtcgacgcg gtgtggaaat agatgggctt g                          41

<210> SEQ ID NO 12
<211> LENGTH: 43
<212> TYPE: DNA
<213> ORGANISM: Primer

<400> SEQUENCE: 12
ggggaattcc cggggatccc atgtcagccc atctttctga atg                        43

<210> SEQ ID NO 13
<211> LENGTH: 47
<212> TYPE: DNA
<213> ORGANISM: Primer

<400> SEQUENCE: 13
ctgacatcgg tcgacgcttt atgaaagaga aggggtttca ccatccc                    47

<210> SEQ ID NO 14
<211> LENGTH: 38
<212> TYPE: DNA
<213> ORGANISM: Primer

<400> SEQUENCE: 14
cccggggatc ccacagttga ttccaccact gatcaacc                              38
```